United States Patent
Lee et al.

(10) Patent No.: US 12,115,093 B2
(45) Date of Patent: Oct. 15, 2024

(54) SOFT ACTUATOR ANKLE SUPPORT ASSEMBLY

(71) Applicants: Hyunglae Lee, Phoenix, AZ (US); Carly Thalman, Tempe, AZ (US); Tiffany Hertzell, Cave Creek, AZ (US); Marielle Debeurre, Scottsdale, AZ (US)

(72) Inventors: Hyunglae Lee, Phoenix, AZ (US); Carly Thalman, Tempe, AZ (US); Tiffany Hertzell, Cave Creek, AZ (US); Marielle Debeurre, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 126 days.

(21) Appl. No.: 17/348,149

(22) Filed: Jun. 15, 2021

(65) Prior Publication Data
US 2021/0386574 A1 Dec. 16, 2021

Related U.S. Application Data

(60) Provisional application No. 63/045,640, filed on Jun. 29, 2020, provisional application No. 63/039,016, filed on Jun. 15, 2020.

(51) Int. Cl.
*A61F 5/01* (2006.01)
*A61B 5/103* (2006.01)
(Continued)

(52) U.S. Cl.
CPC ............ *A61F 5/0111* (2013.01); *A61F 5/012* (2013.01); *A61B 5/1038* (2013.01); *A61B 5/112* (2013.01); *A61F 5/34* (2013.01); *D03D 1/02* (2013.01)

(58) Field of Classification Search
CPC .......... A61F 5/01; A61F 5/0102; A61F 5/012; A61F 5/0127; A61F 5/0195;
(Continued)

(56) References Cited

U.S. PATENT DOCUMENTS 2,694,395 A * 11/1954 Brown ................ A61F 13/085
128/DIG. 20
5,078,128 A * 1/1992 Grim .................... A61F 5/0127
602/23

(Continued)

FOREIGN PATENT DOCUMENTS

| WO | WO-2007008545 A2 * | 1/2007 | ............ A61F 5/0111 |
| WO | WO-2007078845 A2 * | 7/2007 | ............ A61F 5/0104 |
| WO | WO-2013009922 A1 * | 1/2013 | ............ A61F 5/0113 |

OTHER PUBLICATIONS

Asbeck, R.J. Dyer, A.F. Larusson, and C.J. Walsh. Biologicallyinspired soft exosuit. In 2013 IEEE 13th International Conference on Rehabilitation Robotics (ICORR), pp. 1-8, 2013.
(Continued)

*Primary Examiner* — Keri J Nelson
*Assistant Examiner* — Seth R. Brown
(74) *Attorney, Agent, or Firm* — Michael Best & Friedrich LLP

(57) ABSTRACT

An ankle support assembly includes a body having a plurality of fabric layers. The body extends along a longitudinal axis. A sealed, inflatable chamber is supported by the body. A valve member is supported by the body and in fluid communication with the chamber. A plurality of retaining members are positioned relative to the chamber. The retaining members are spaced apart from each other. The retaining members are configured to limit expansion of the chamber in at least one direction. The retaining members are positioned relative to the chamber such that the body has a
(Continued)

variable stiffness along the longitudinal axis when the chamber is inflated.

18 Claims, 22 Drawing Sheets

(51) Int. Cl.
    *A61B 5/11*           (2006.01)
    *A61F 5/34*           (2006.01)
    *D03D 1/02*          (2006.01)

(58) Field of Classification Search
    CPC .......... A61F 5/05816; A61F 5/34; A61F 5/30; A61F 5/0104–0118; A61F 5/05; D03D 1/02; A61B 5/1038; A61B 5/112; A61B 17/132; A61B 17/135; A61B 17/1322
    USPC ......... 602/13, 5, 12, 23, 27; 128/118.1, 882; 606/201–203
    See application file for complete search history.

(56) References Cited

U.S. PATENT DOCUMENTS

| | | | |
|---|---|---|---|
| 5,288,286 A * | 2/1994 | Davis | A61F 5/0111 602/5 |
| 6,945,944 B2 * | 9/2005 | Kuiper | A61F 5/0104 602/5 |
| 2004/0236258 A1 * | 11/2004 | Burns | A61F 5/012 602/13 |
| 2006/0173393 A1 * | 8/2006 | Sailhen | A61F 5/012 602/23 |
| 2012/0253250 A1 * | 10/2012 | Spahn | A61F 5/0127 602/13 |
| 2019/0336315 A1 * | 11/2019 | Polygerinos | A61H 1/0266 |
| 2020/0376650 A1 * | 12/2020 | Polygerinos | B25J 9/142 |

OTHER PUBLICATIONS

Bao, H. Fang, L. Chen, Y. Wan, F. Xu, Q. Yang, and L. Zhang. Soft robotics: Academic insights and perspectives through bibliometric analysis. Soft Robotics, 5(3):229-241, 2018.

Browning, J. R. Modica, R. Kram, and A. Goswami. The effects of adding mass to the legs on the energetics and biomechanics of walking. Medicine & Science in Sports & Exercise, 39(3):515-525, 2007.

Yeung, Kai-Ming Chan, CH So, and WY Yuan. An epidemiological survey on ankle sprain. British journal of sports medicine, 28(2):112-116, 1994.

Chung, R. Heimgartner, C. T. O'Neill, N. S. Phipps, and C. J. Walsh. Exoboot, a soft inflatable robotic boot to assist ankle during walking: Design, characterization and preliminary tests. In 2018 7th IEEE International Conference on Biomedical Robotics and Biomechatronics (Biorob), pp. 509-516. IEEE, 2018.

Cianchetti, C. Laschi, A. Menciassi, and P. Dario. Biomedical applications of soft robotics. Nature Reviews Materials, 3 (6):143-153, 2018.

Cowper, "The shear coefficient in timoshenko's beam theory," Journal of Applied Mechanics, pp. 335-340, 1966.

Ding et al., "Pneumatic Energy Sources for Autonomous and Wearable Soft Robotics," Soft Robotics, vol. 2, No. 00, 2014.

Garrick. The frequency of injury, mechanism of injury, and epidemiology of ankle sprains. The American journal of sports medicine, 5(6):241-242, 1977.

Geboers, M R Drost, F Spaans, H Kuipers, and H A Seelen. Immediate and long-term effects of ankle-foot orthosis on muscle activity during walking: a randomized study of patients with unilateral foot drop. Archives of physical medicine and rehabilitation, 83(2):240-245, 2002.

Jaivin, J. O Bishop, W G Braly, and H S Tullos. Management of acquired adult dropfoot. Foot & ankle, 13(2):98-104, 1992.

Jiang and N. Gravish. Sliding-layer laminates: a robotic material enabling robust and adaptable undulatory locomotion. In 2018 IEEE/RSJ International Conference on Intelligent Robots and Systems (IROS), pp. 5944-5951. IEEE, 2018.

Kluding, K. Dunning, M. W O'dell, S. S Wu, J. Ginosian, J. Feld, and K. McBride. Foot drop stimulation versus ankle foot orthosis after stroke: 30-week outcomes. Stroke, 44(6):1660-1669, 2013.

Kwon, J. Park, S. Ku, Y. Jeong, N. Paik, and Y.L. Park. A Soft Wearable Robotic Ankle-Foot-Orthosis for Post-Stroke Patients. IEEE RA-L, International Conference on Soft Robotics (RoboSoft), 2019.

Kwon, S. Yoon, and Y. Park. Flat inflatable artificial muscles with large stroke and adjustable force-length relations. IEEE Transactions on Robotics, 2020.

Lee, S. Crea, P. Malcolm, I. Galiana, A. Asbeck, and C. Walsh. Controlling negative and positive power at the ankle with a soft exosuit. In IEEE International Conference on Robotics and Automation (ICRA), pp. 3509-3515. IEEE, 2016.

Lehmann, S. M Condon, B. J de Lateur, and J C Smith. Ankle-foot orthoses: effect on gait abnormalities in tibial nerve paralysis. Archives of physical medicine and rehabilitation, 66(4):212-218, 1985.

Malcolm, S Lee, S Crea, C Siviy, F Saucedo, I Galiana, F A Panizzolo, K G Holt, and C J Walsh. Varying negative work assistance at the ankle with a soft exosuit during loaded walking. Journal of neuroengineering and rehabilitation, 14(1):62, 2017.

Malcolm, W Derave, S Galle, and D De Clercq. A simple exoskeleton that assists plantarflexion can reduce the metabolic cost of human walking. PloS one, 8(2), 2013.

Mueller, S D Minor, J A Schaaf, M J Strube, and S A Sahrmann. Relationship of plantar-flexor peak torque and dorsiflexion range of motion to kinetic variables during walking. Physical therapy, 75(8):684-693, 1995.

Nalam and H. Lee. Design and validation of a multi-axis robotic platform for the characterization of ankle neuromechanics. In 2017 IEEE International Conference on Robotics and Automation (ICRA), pp. 511-516. IEEE, 2017.

Park, B.R. Chen, N.O. Perez-Arancibia, D. Young, L. Stirling, R.J. Wood, E.C. Goldfield, and R. Nagpal. Design and control of a bio-inspired soft wearable robotic device for ankle-foot rehabilitation. Bioinspiration & biomimetics, 9(1):016007, 2014.

Ren, Y. Wu, C. Yang, T. Xu, R. L. Harvey, and L. Zhang. Developing a Wearable Ankle Rehabilitation Robotic Device for inBed Acute Stroke Rehabilitation. IEEE Transactions on Neural Systems and Rehabilitation Engineering, 2017.

Shi, X Chen, Z Yue, S Yin, Q Weng, X Zhang, J Wang, and W Wen. Wearable ankle robots in post-stroke rehabilitation of gait: A systematic review. Frontiers in neurorobotics, 13:63, 2019.

Stein, D G Everaert, A K Thompson, S Chong, M Whittaker, J Robertson, and G Kuether. Long-term therapeutic and orthotic effects of a foot drop stimulator on walking performance in progressive and nonprogressive neurological disorders. Neurorehabilitation and neural repair, 24(2):152-167, 2010.

Sun, Y Chen, T Han, C Jiao, B Lian, and Y Song. A soft gripper with variable stiffness inspired by pangolin scales, toothed pneumatic actuator and autonomous controller. Robotics and Computer-Integrated Manufacturing, 61:101848, 2020.

Thalman and H Lee. Design and validation of a soft robotic ankle-foot orthosis (sr-afo) exosuit for inversion and eversion ankle support. In 2019 International Conference on Robotics and Automation (ICRA). IEEE, 2020.

Thalman et al., "The Multi-material Actuator for Variable Stiffness (MAVS): Design, Modeling, and Characterization of a Soft Actuator for Lateral Ankle Support," 2020 IEEE/RSJ International Conference on Intelligent Robots and Systems (IROS) Oct. 25-29, 2020, Las Vegas, NV, USA.

Thalman, J. Hsu, L. Snyder, and P. Polygerinos. Design of a soft ankle-foot orthosis exosuit for foot drop assistance. In 2019 International Conference on Robotics and Automation (ICRA), pp. 8436-8442. IEEE, 2019.

(56) References Cited

OTHER PUBLICATIONS

Thalman, T Hertzell, and H Lee. Toward a soft robotic ankle-foot orthosis (sr-afo) exosuit for human locomotion: Preliminary results in late stance plantarflexion assistance. In IEEE International Conference on Soft Robotics, (RoboSoft). IEEE, 2020.

Thomas et al., "Inflatable beams subjected to axial forces," Proceedings of the TensiNet Symposium, Jun. 3-5, 2019, Politecnico di Milano, Milan, Italy, pp. 160-171.

Venesky, C. L Docherty, J. Dapena, and J. Schrader. Prophylactic ankle braces and knee varus-valgus and internal-external rotation torque. Journal of athletic training, 41(3):239, 2006.

Wielgosz and J-C Thomas. Deflections of inflatable fabric panels at high pressure. Thin-walled structures, 40(6):523-536, 2002.

Wielgosz, JC Thomas, and A Le Van. Mechanics of inflatable fabric beams. In International Conference on Computational & Experimental Engineering and Sciences Honolulu, Hawaii, USA, 2008.

Wiszomirska, M. Błazkiewicz, K. Kaczmarczyk, G. Brzuszkiewicz-Kuzmicka, and A Wit. Effect of drop foot on spatiotemporal, kinematic, and kinetic parameters during gait. Applied bionics and biomechanics, 2017.

* cited by examiner

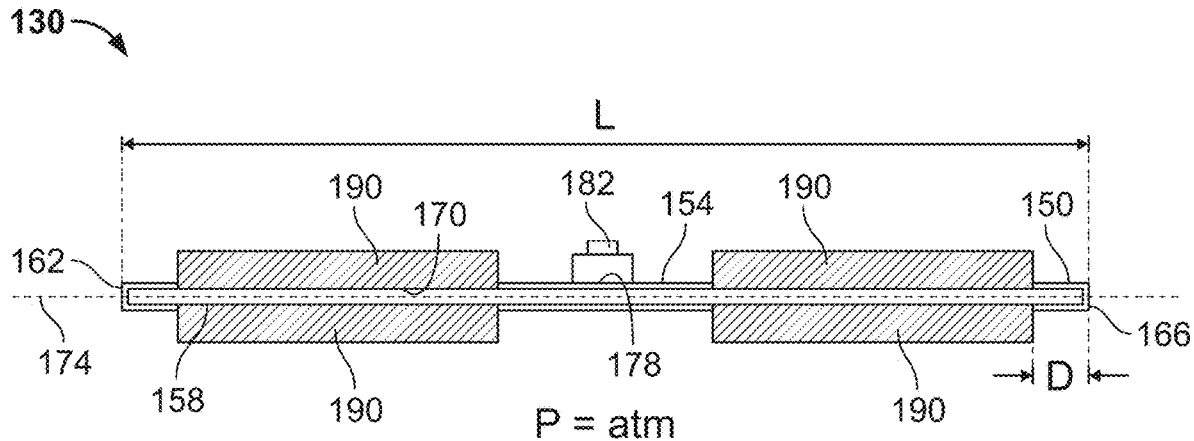
FIG. 3A
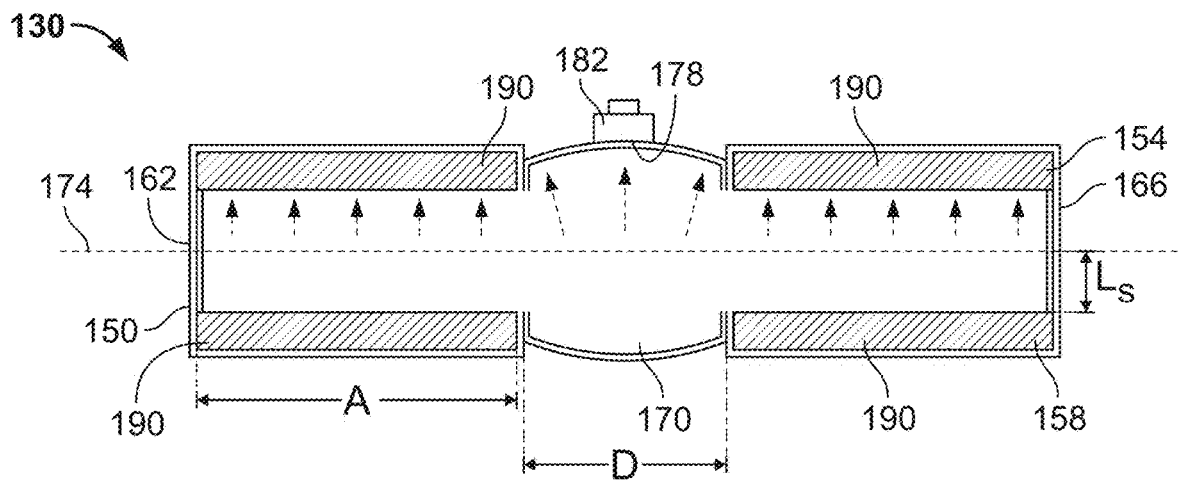
FIG. 3B
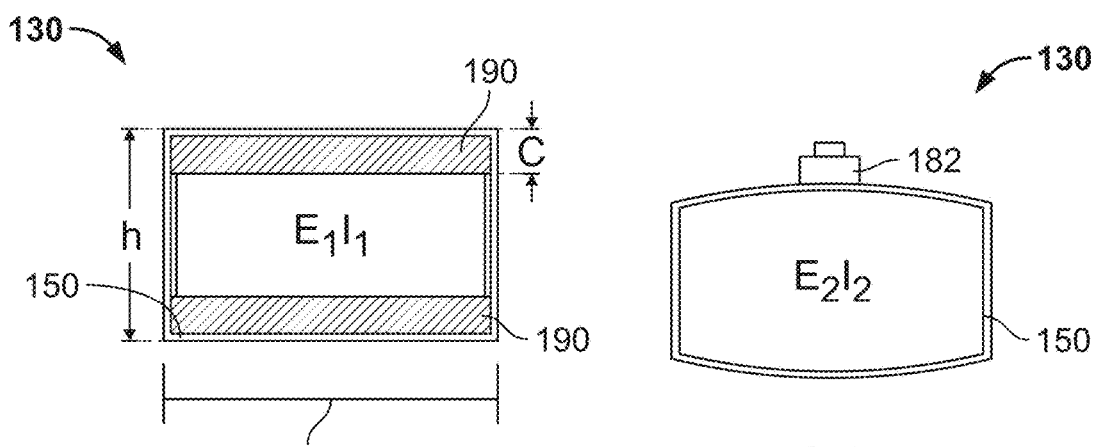
FIG. 3C
FIG. 3D

P = atm

P > atm

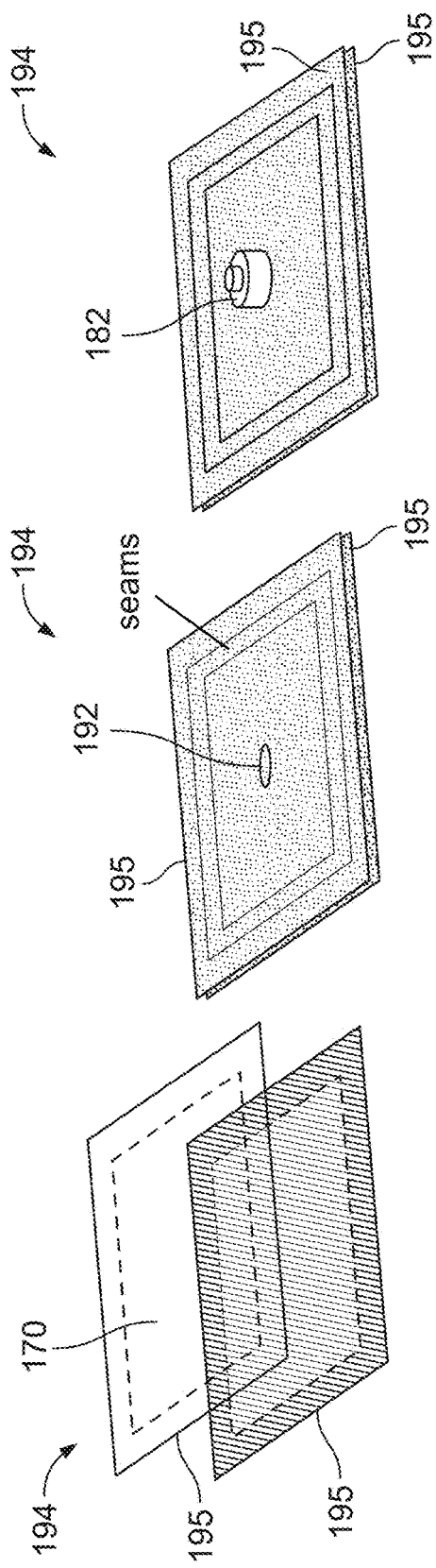
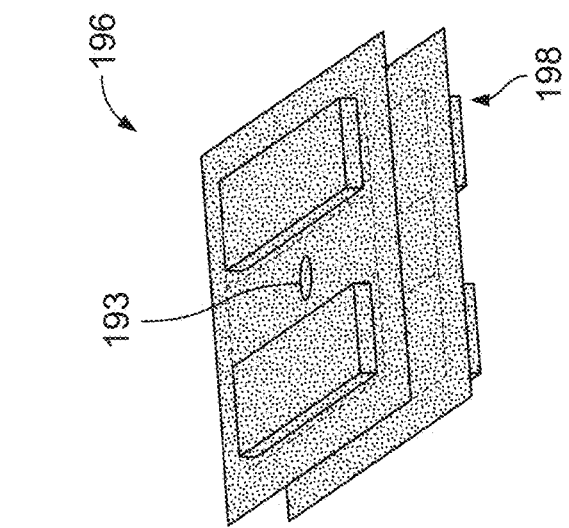
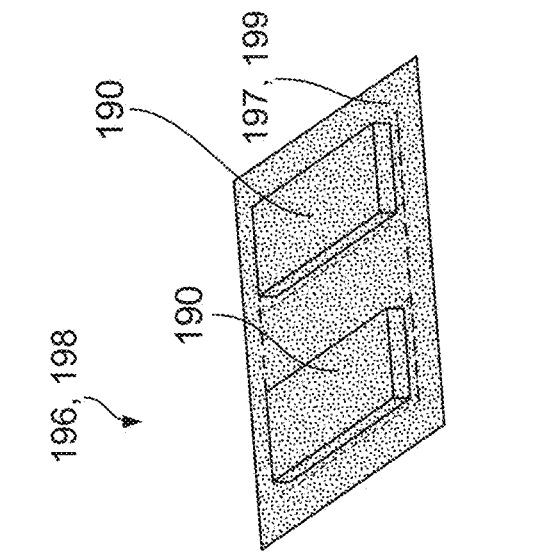
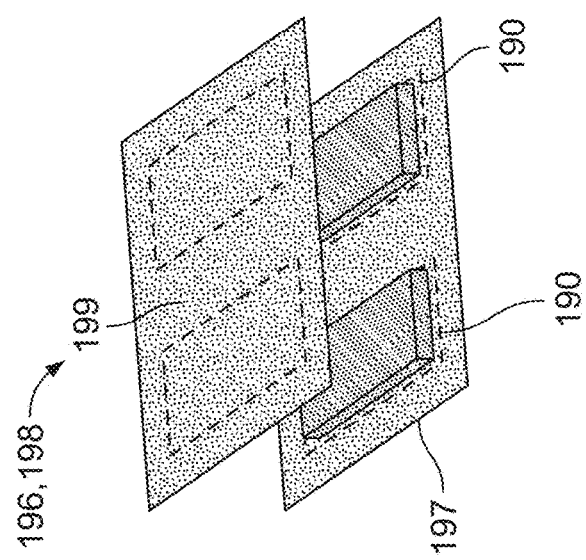

30 ↙

Step: Pressure

Step: Transverse Load

Multi-Material Actuator for Variable Stiffness
MAVS

Stiffening – Buckling Resistance

Deflated
P = 0

Inflated   Compliant
P > 0      Region (s)

Rigid
Retainer (s)

Use-Case Example of MAVS

Deflated      MAVS
P = 0

Hinge Joint

Inflated      Torque
P > 0         (T)

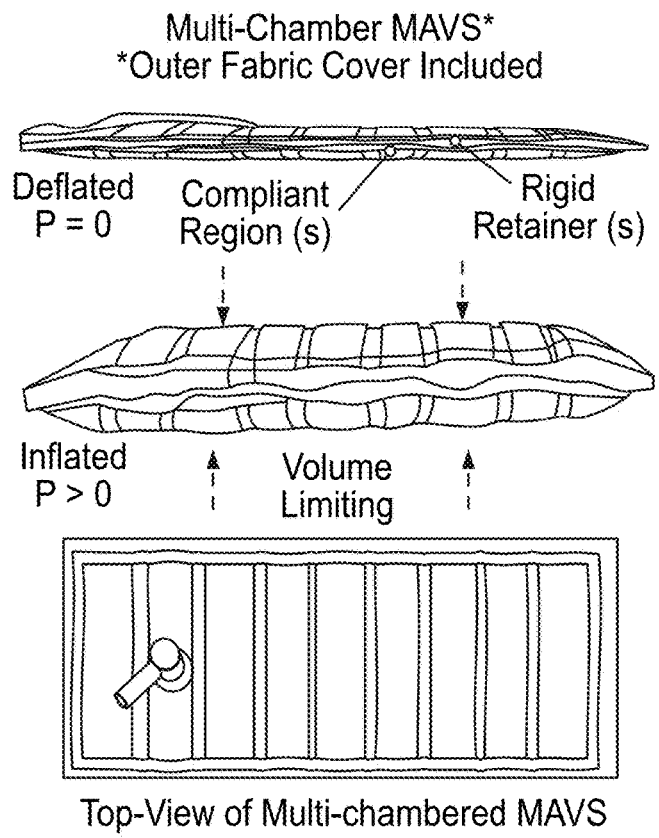
FIG. 17
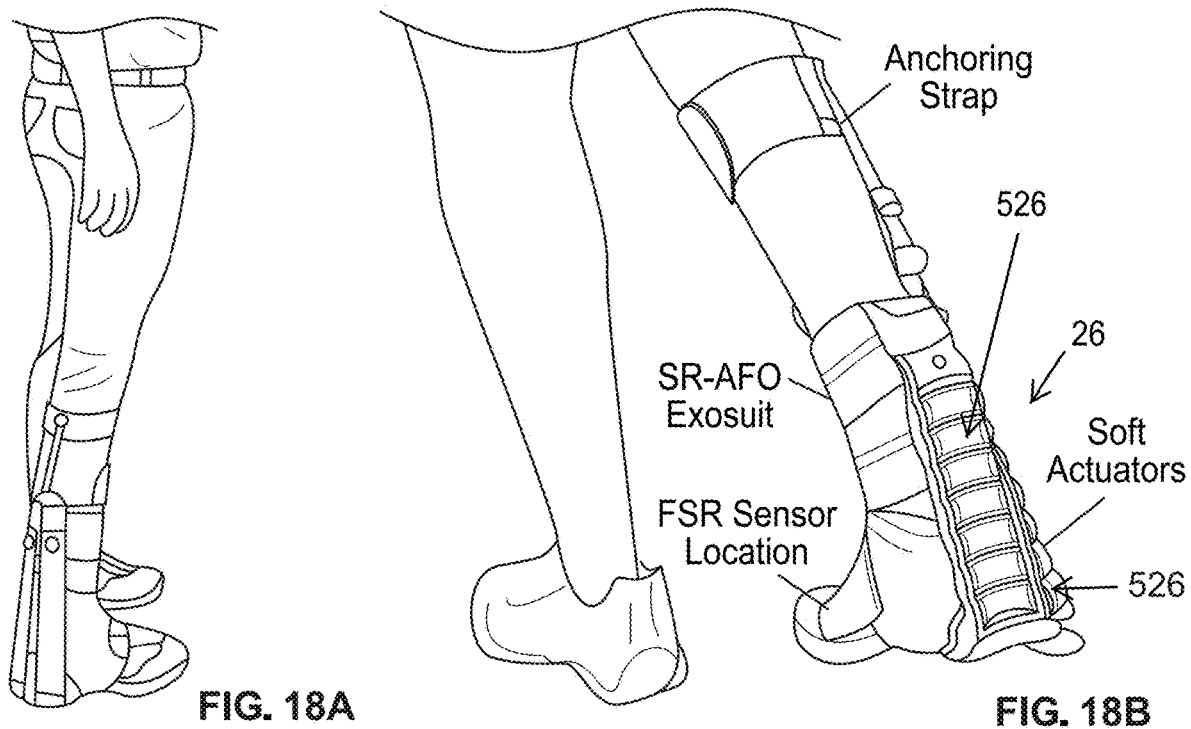
FIG. 18A
FIG. 18B

SOFT ACTUATOR ANKLE SUPPORT ASSEMBLY

CROSS-REFERENCE TO RELATED APPLICATIONS

This application is a non-provisional of and claims the benefit of U.S. Provisional Patent Application No. 63/045,640, filed Jun. 29, 2020, and U.S. Provisional Patent Application No. 63/039,016, filed Jun. 15, 2020, the contents of each of which are incorporated herein by reference.

STATEMENT REGARDING FEDERALLY SPONSORED RESEARCH OR DEVELOPMENT

This invention was made with government support under 1841051 awarded by the National Science Foundation. The Government has certain rights in the invention.

FIELD

The present disclosure relates to a fabric-based inflatable actuator or soft actuator, and more specifically, to a soft actuator ankle support assembly.

BACKGROUND

Permanent deformation of the tendons surrounding the ankle joint can occur in individuals suffering from chronic ankle instability (CAI), which is a long-term disability that often arises as a result of recurrent ankle sprains. Lateral ankle buckling causes sudden instances of ankle inversion-eversion (IE) in the frontal plane, which creates excessive stress in the tendons and results in the ankle sprain. An estimated 85% of reported ankle sprains are a result of such injuries, and repeated occurrences of sprained ankles can lead to CAI. An affected individual is at an increased risk of injury, trips, and falls with the onset of CAI, as the damaged tendons surrounding the ankle joint may lead to an irregular gait pattern. Additionally, the ankle joint is responsible for 45% of the power behind human locomotion, and plantarflexion is a critical motion throughout the entire gait cycle. Body propulsion during a forward gait requires a propulsive force that pushes off of the ground and creates forward motion. Individuals suffering from hemiparesis after a stroke, paralysis of pretibial muscles, or fixed plantarflexion will often experience a lack of shock absorption and loss of definitive heel strike. This can cause a loss of the final rocker action needed to propel the foot forward for toe-off to transition to pre-swing. As a result, various forms of gait abnormalities arise that can cause further injury, pain, or risk of trips and falls.

SUMMARY

In one embodiment, an ankle support assembly includes a body having a plurality of fabric layers. The body extends along a longitudinal axis. A sealed, inflatable chamber is supported by the body. A valve member is supported by the body and in fluid communication with the chamber. A plurality of retaining members are positioned relative to the chamber. Each of the retaining members is spaced apart from each other. The retaining members are configured to limit expansion of the chamber in at least one direction. The retaining members are positioned relative to the chamber such that the body has a variable stiffness along the longitudinal axis when the chamber is inflated.

In another embodiment, an ankle support assembly includes a frame, and a support member positionable by the frame relative to an ankle of a user. The support member includes a body having a plurality of fabric layers. The body extends along a longitudinal axis. A sealed, inflatable chamber is supported by the body. A valve member is supported by the body and in fluid communication with the chamber. The valve member is configured to be coupled to a hose for inflating the chamber. A plurality of retaining members are positioned relative to the chamber. The retaining members are spaced apart from each other. The retaining members are configured to limit expansion of the chamber in at least one direction. The support member is configured as a fabric-based actuator. The retaining members are positioned relative to the chamber such that the body has a variable stiffness along the longitudinal axis when the chamber is inflated. The support member is configured to provide support in at least one directional movement of the ankle.

In yet another embodiment, a method of manufacturing an ankle support assembly includes forming a first layer having a sealed, inflatable chamber. Forming the first layer includes heat-sealing pieces of fabric to create an air-tight seal. The method further includes forming a second layer and securing a first plurality of retaining members to the second layer. The method further includes forming a third layer and securing a second plurality of retaining members to the third layer, and creating a hole in the third layer. The method further includes connecting a valve member to the chamber, and stacking the first, second, and third layers together such that the first layer is between the second layer and the third layer. The method further includes aligning the hole of the third layer with the valve member such that the valve member extends through the hole to be accessible to a user, and stitching the first, second, and third layers together.

In yet another embodiment, an ankle support assembly includes a first, inflatable support member configured to provide inversion/eversion support for an ankle, the first support member formed form layers of fabric and having at least one rigid retaining member coupled to the layers of fabric. The ankle support assembly further includes a second, inflatable support member configured to provide plantarflexion support for the ankle, the second support member formed from additional layers of fabric and having heat seals that form air chambers along the second support member.

Other aspects of the disclosure will become apparent by consideration of the detailed description and accompanying drawings.

BRIEF DESCRIPTION OF THE DRAWINGS

FIGS. 3A-3D are schematic views of a support member according to a first embodiment, for providing inversion/eversion support, with FIG. 3A illustrating a side profile deflated, FIG. 3B illustrating a side profile inflated, FIG. 3C illustrating a rigid cross-section, and FIG. 3D illustrating a soft cross-section.

FIGS. 6A-6H illustrate a method to manufacture the support member of FIGS. 4-5.

FIGS. 10A-10E and 11-17 provide additional details regarding the support member of FIGS. 1, 2, 3A-3D, 4, 5, 6A-6H, 7, 8A-8F, and 9A-9C for providing inversion/eversion support, including details regarding testing that was conducted on the support member.

FIGS. 18A-18B are perspective views of an ankle support assembly according to another embodiment, having a support member for providing plantarflexion support.

Before any embodiments of the disclosure are explained in detail, it is to be understood that the disclosure is not limited in its application to the details of embodiment and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical or hydraulic connections or couplings, whether direct or indirect.

DETAILED DESCRIPTION

Figure 1:
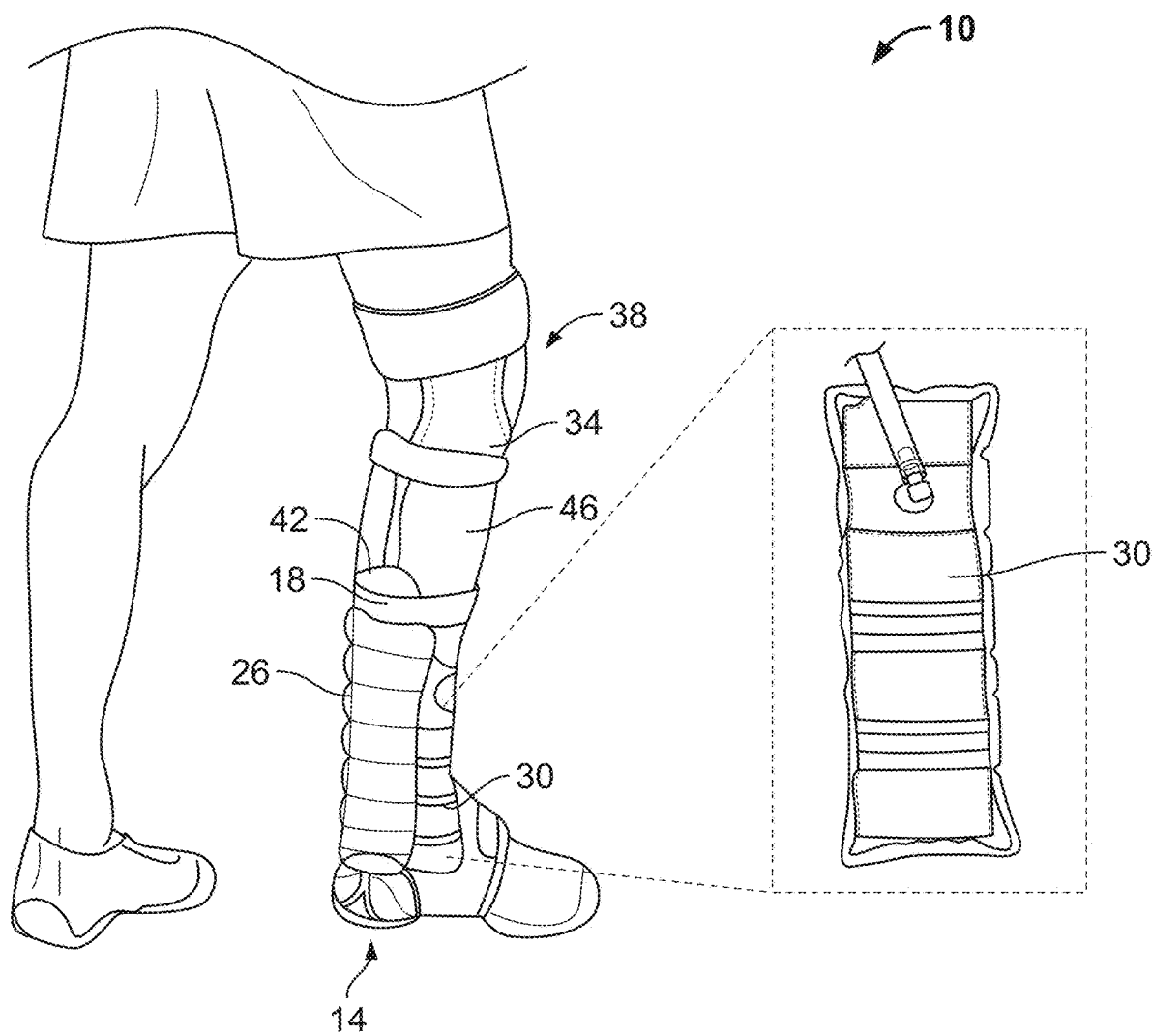
FIG. 1 is a perspective view of an ankle support assembly, illustrating a frame and a support member supported by the frame.

FIG. 1 illustrates an ankle support assembly 10 wearable by a user for providing select support to a user's ankle 14 during use (e.g., walking, running, etc.). The ankle support assembly 10 includes a frame 18 (e.g., exosuit) and a plurality of support members 26, 30 supported by the frame 18. The support members 26, 30 are selectively positioned on the frame 18 for providing support in select directions of movement of the ankle 14 (e.g., plantar flexion/dorsiflexion, inversion/eversion, etc.). The illustrated ankle support assembly 10 includes the frame 18, a first support member 26 (e.g., a contracting soft actuator to support plantarflexion), and a second support member 30 (e.g., a soft actuator with rigid retaining members to support inversion/eversion). In other embodiments only a single support member (e.g., support member 30, or support member 26) may be provided, or other numbers of support members 26, 30 than that shown may be provided. The frame 18 includes an anchoring strap 34 positioned on a user's knee 38, and a connecting member 42 (e.g., strap) extending between the anchoring strap 34 and the first support member 26. In other embodiments, the ankle support assembly 10 may include other numbers and arrangements of support members 26, 30 (e.g., only a single support member or more than two support members). Additionally, in other embodiments the ankle support assembly 10 includes other numbers and arrangements of anchoring straps 34 and connecting members 42. For example, in some embodiments the ankle support assembly 10 does not include an anchoring strap 34 and/or connecting member 42.

With continued reference to FIG. 1, the illustrated first support member 26 is positioned to provide support to the ankle 14 in the direction of the plantar flexion and dorsiflexion movement of the ankle 14. The illustrated second support member 30 is positioned to provide support to the ankle 14 in the inversion-eversion (IE) direction during movement of the ankle 14. The anchoring strap 34 is configured to maintain the frame 18 on a user's body part (e.g., leg 46). In other embodiments, the support members 26, 30 may be used in other body part support assemblies (e.g., wrist support assembly, etc.).

Figure 2:
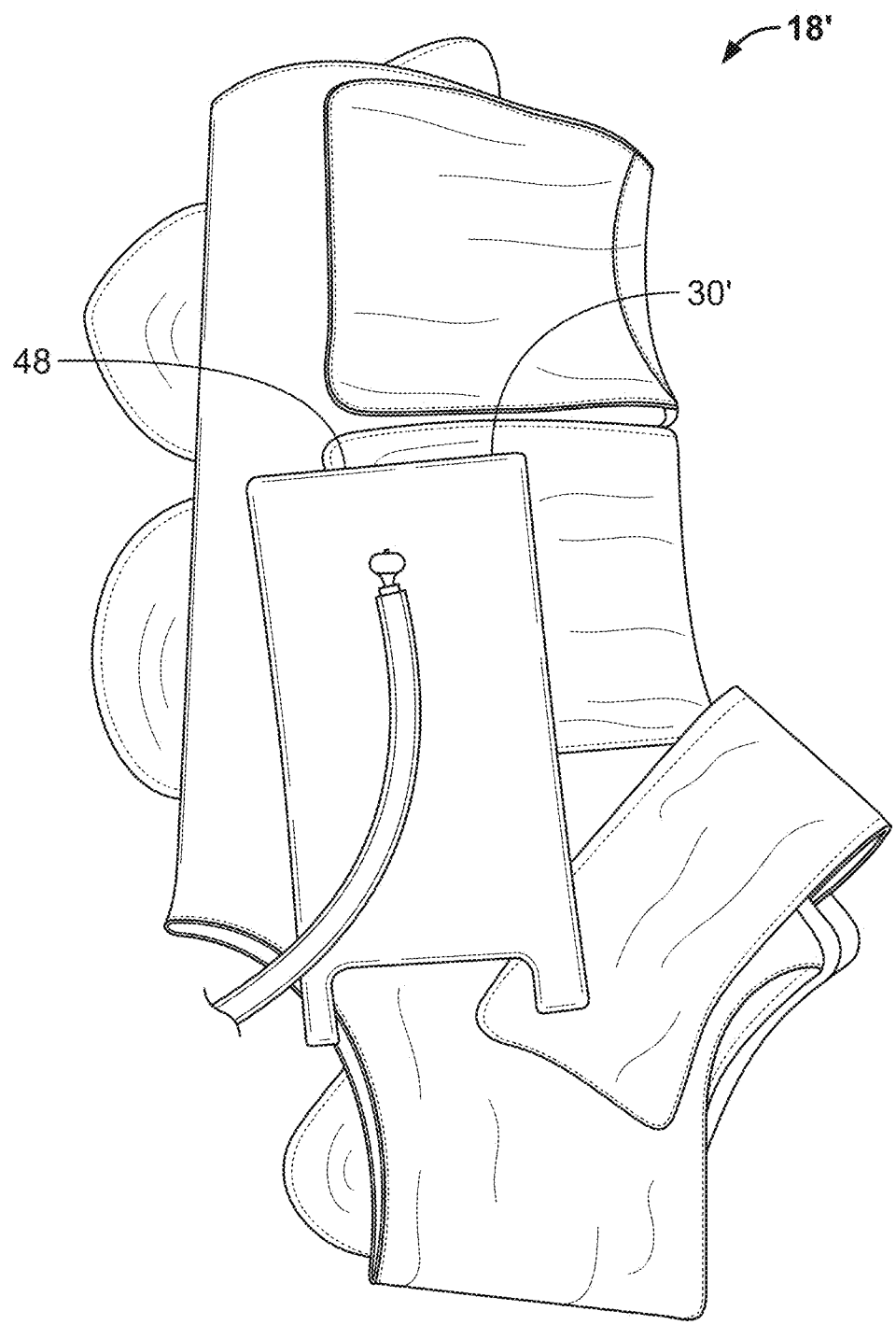
FIG. 2 is a perspective view of an example of the frame of FIG. 1.

FIG. 2 illustrates one example of the frame 18' of the ankle support assembly 10 of FIG. 1, including the second support member 30'. In particular, the frame 18' includes a pocket 48, and the second support member 30' is received in the pocket 48.

FIGS. 3A-3D schematically illustrate a support member 130 according to a first embodiment (e.g., for use as the second support member 30 in FIG. 1, to provide inversion/eversion support). The support member 130 includes a body 150 having a first side portion 154, a second side portion 158, and a first end portion 162 and a second end portion 166 extending between the first and second side portions 154, 158, respectively. The first and second side portions 154, 158 and the first and second end portions 162, 166 define a chamber 170 therebetween. The chamber 170 is configured to receive a fluid (e.g., air). The support member 130 includes a longitudinal axis 174 extending through the first end portion 162 and the second end portion 166 of the body 150. As such, the body 150 is elongated along the longitudinal axis 174.

The support member 130 includes an inlet 178 and a valve member 182 positioned at the inlet 178. The valve member 182 is in fluid communication with the chamber 170. In the illustrated embodiment, the inlet 178/valve member 182 is supported by the first side portion 154. In other embodiments, the inlet 178/valve member 182 is positioned at other locations on the body 150 (e.g., second side portion 158, end portions 162, 166, etc.). The valve member 182 is connectable to a tube or hose 186 (FIG. 4A) for selectively inflating the chamber 170.

The support member 130 further includes a plurality of retaining members 190 coupled to the body 150 (e.g., the first side portion 154 and the second side portion 158). The retaining members 190 are rigid. The retaining members 190 are configured to limit the expansion of the chamber 170 in select directions (e.g., upward or downward from the frame of reference of FIG. 3B) to physically restrict a volume of the chamber 170 when the chamber 170 is being inflated. Accordingly, the support member 130 is configured as a fabric-based inflatable actuator, which may also be referred to as a "soft" actuator herein.

With continued reference to FIGS. 3A-3D, in the illustrated embodiment, the support member 130 includes four retaining members 190. Two of the retaining members 190 are positioned on one side of the longitudinal axis 174 and supported by the first side portion 154, and the remaining two retaining members 190 are positioned on the opposite side of the longitudinal axis 174 and supported by the second side portion 158. Each retaining member 190 is positioned proximate one of the first end portion 162 and the second end portion 166. Furthermore, the illustrated retaining members 190 are vertically aligned with respect to the longitudinal axis 174. In other words, each of the retaining members 190 are spaced vertically equidistant relative to the longitudinal axis 174 as viewed in FIGS. 3A and 3B.

With continued reference to FIGS. 3A-3D, each retaining member 190 has a length A, a width B, and a thickness C with respect to the longitudinal axis 174 (FIGS. 3B and 3C). Each illustrated retaining member 190 has a rectangular shape having the same length A, width B, and thickness C. As such, the retaining members 190 have the same shape and size. In other embodiments, the shape, size, or both of some or all of the retaining members 190 may be different. In addition, the support member 130 may include other numbers of retaining members 190, and/or the total shape and total size (e.g., length L, height h, etc.) of the support member 130 may be adjustable.

Figure 7:
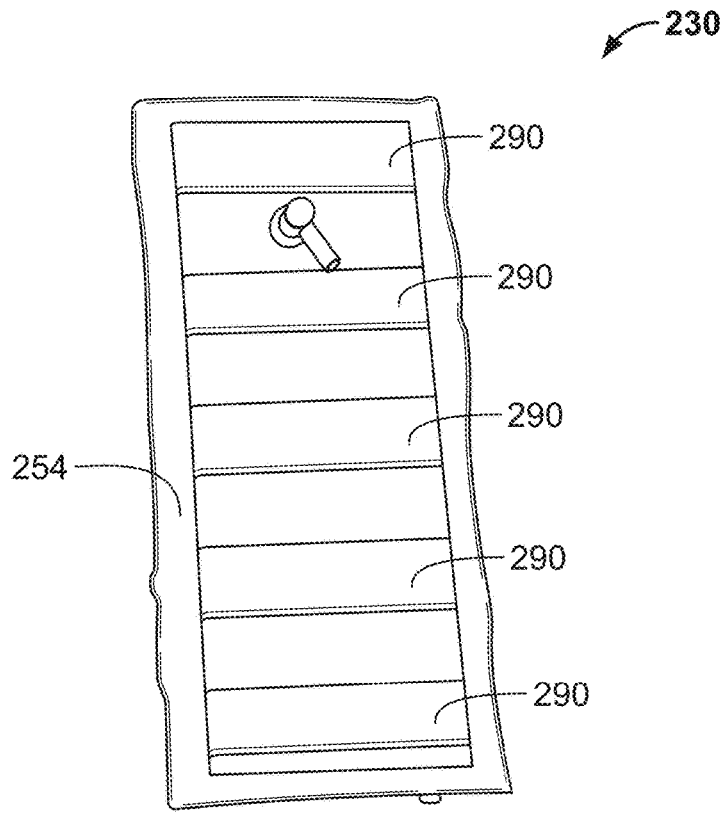
FIG. 7 is a perspective view of another example of the support member of FIGS. 3A-3D.
Figures 8A, 8B, 8C, 8D, 8E, 8F:
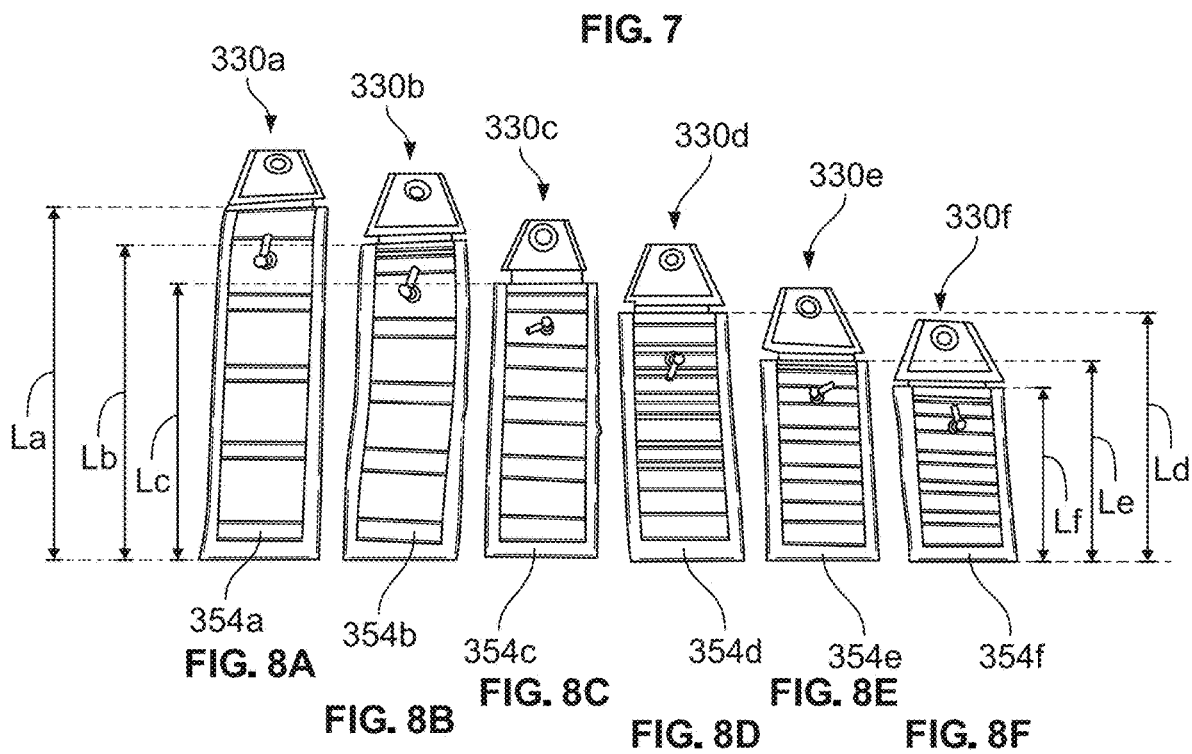
FIGS. 8A-8F are perspective views of other examples of the support member of FIGS. 3A-3D.
Figure 9A:
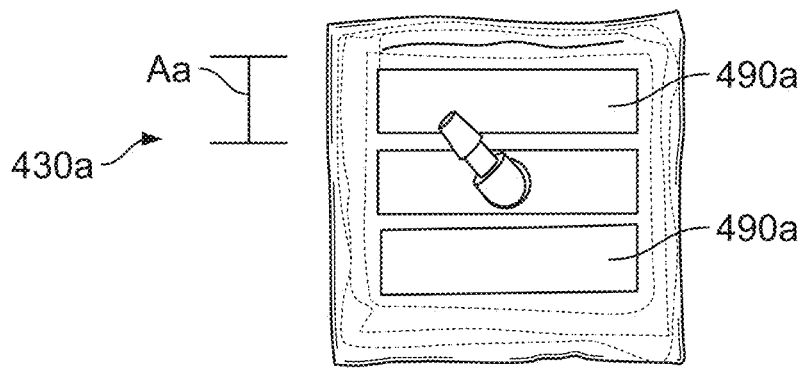
FIGS. 9A-9C are perspective views of yet other examples of the support member of FIGS. 3A-3D.
Figure 9B:
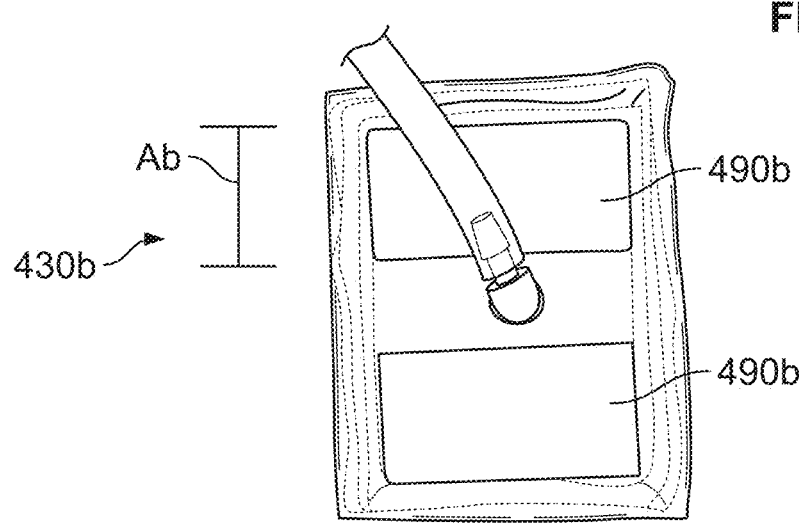
Figure 9C:
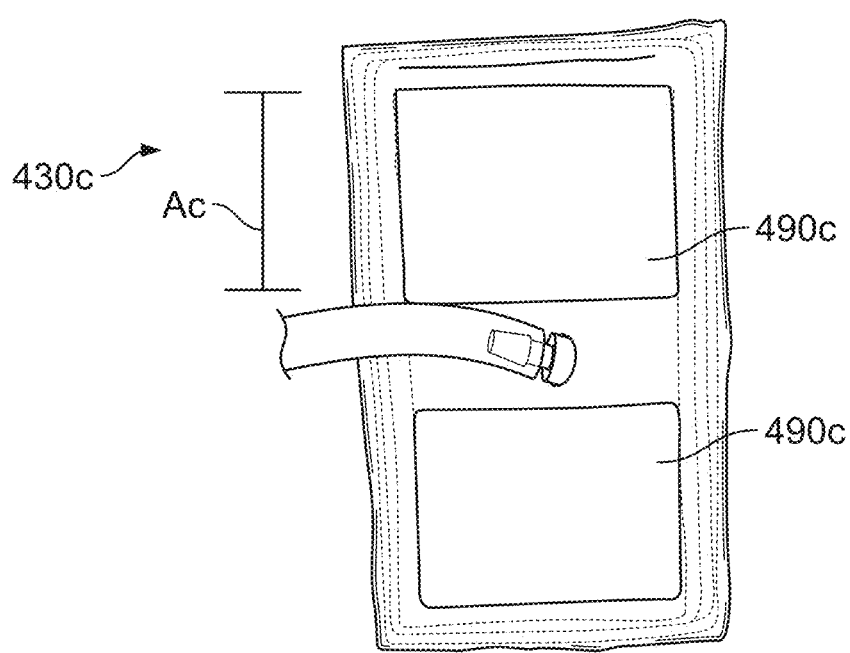
Figure 10A:
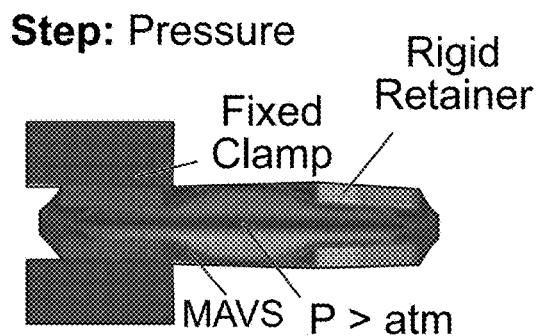
Figure 10B:
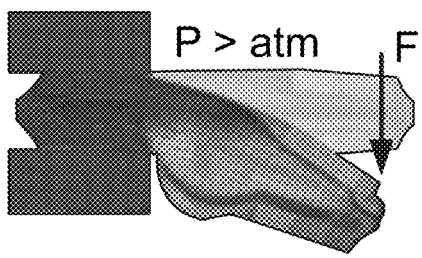
Figure 10C:
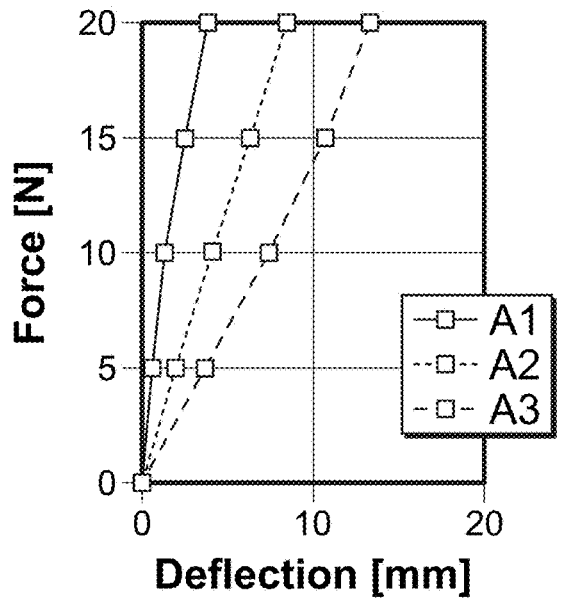
Figure 10D:
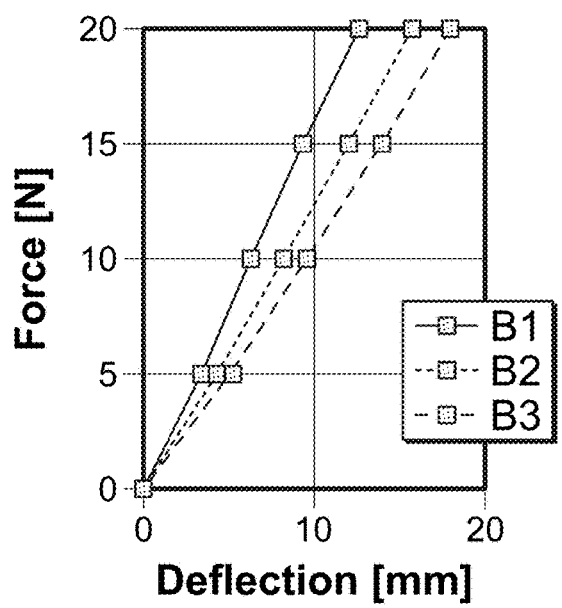
Figure 10E:
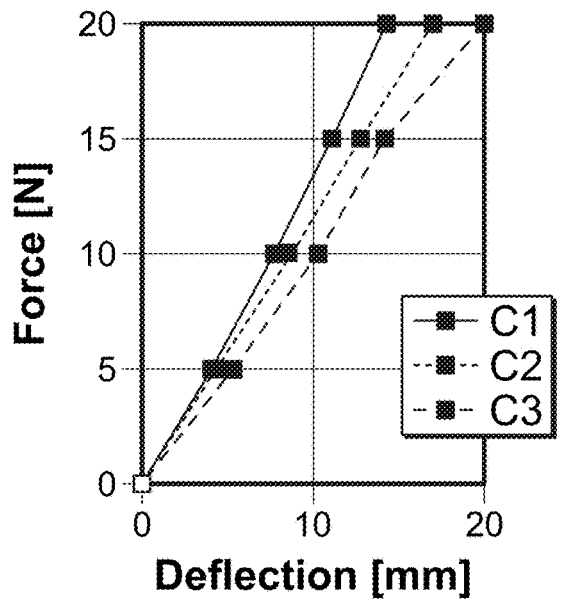
Figure 11:
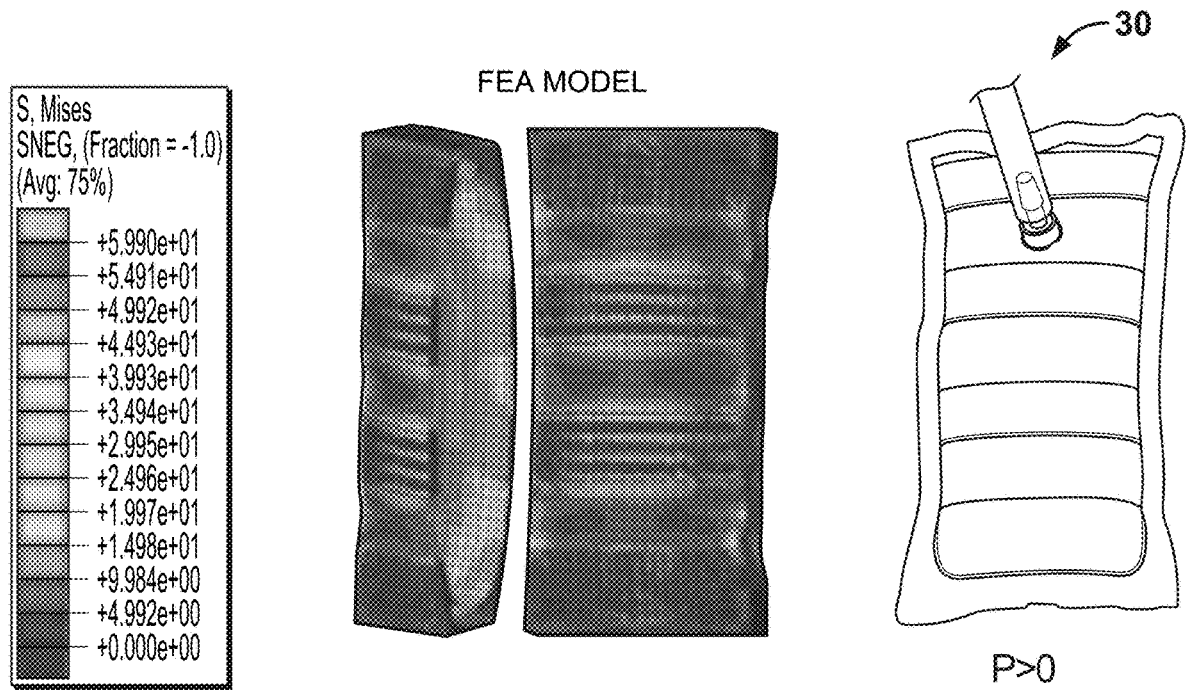
Figure 12:
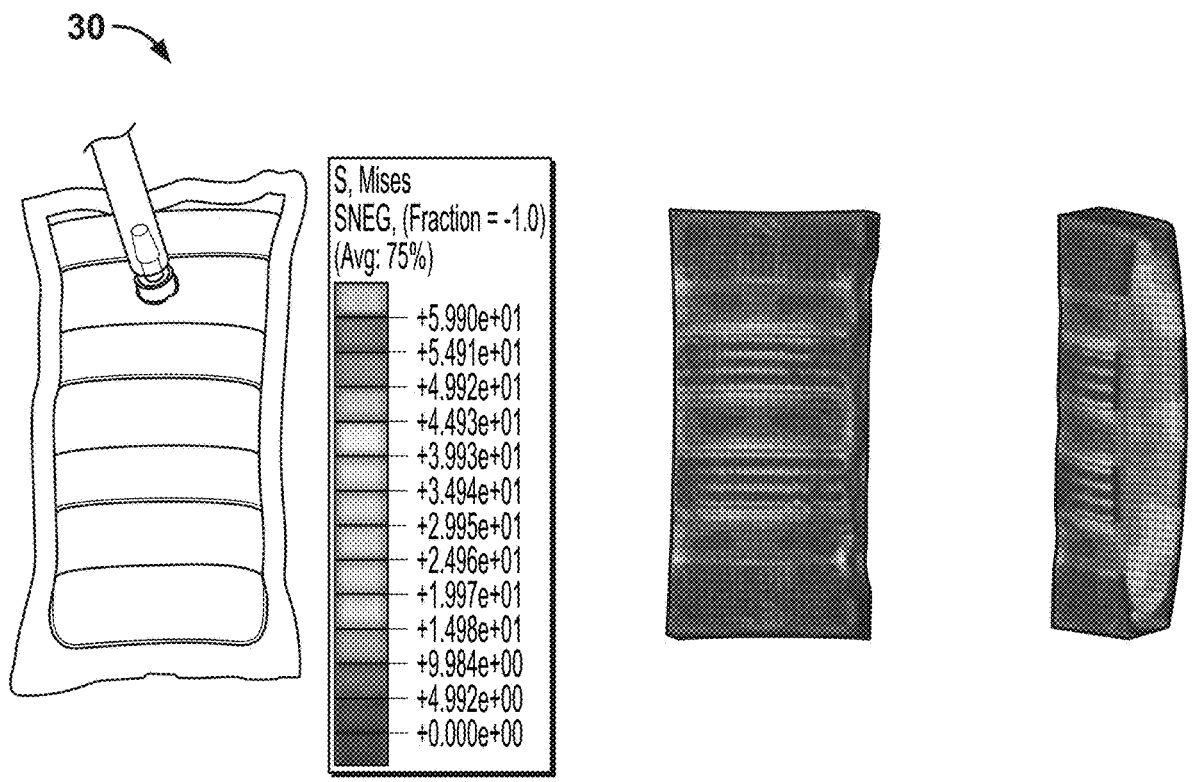
Figure 13:
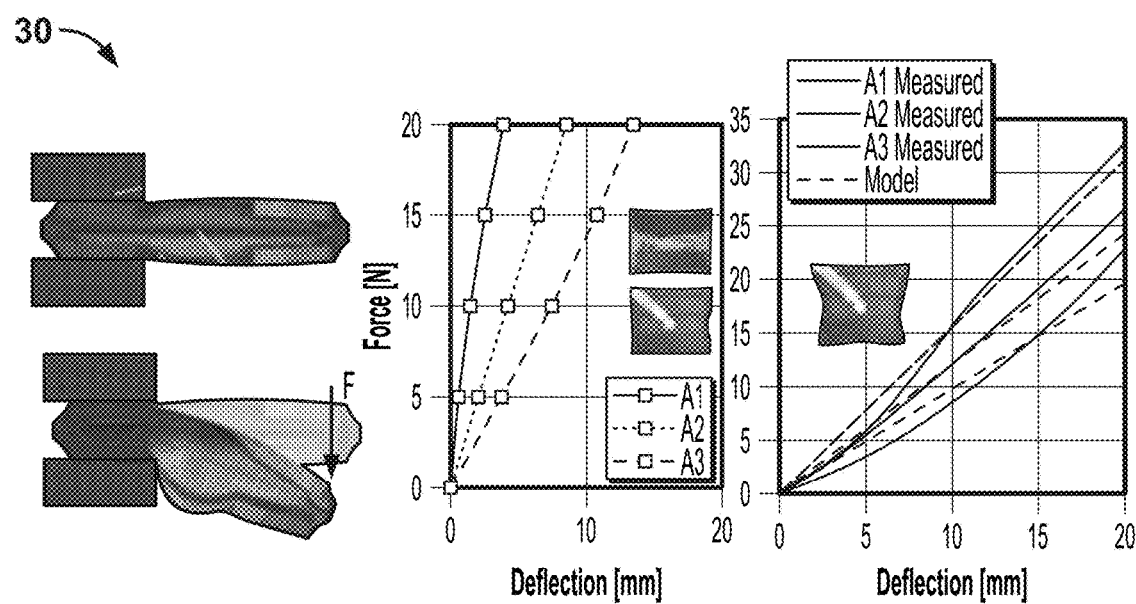
Figure 14:
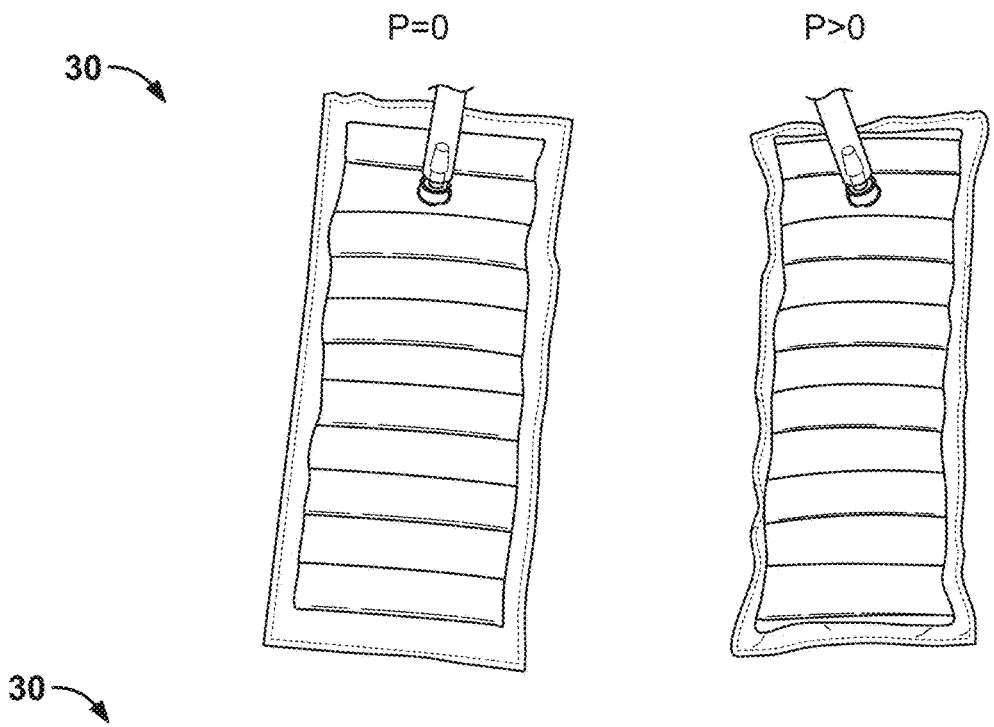
Figure 15:
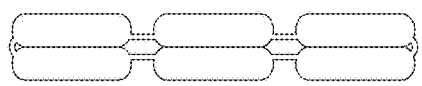
Figure 15:
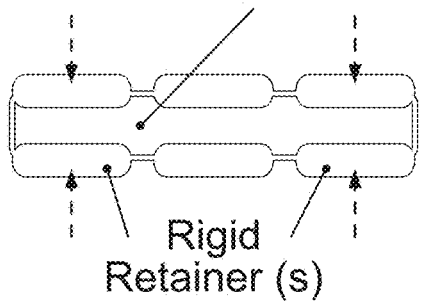
Figure 15:
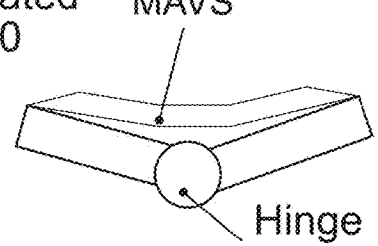
Figure 15:
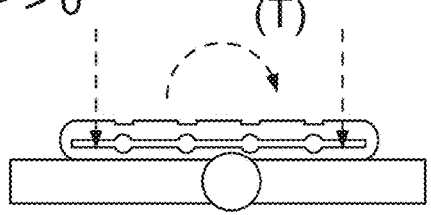
Figure 16:
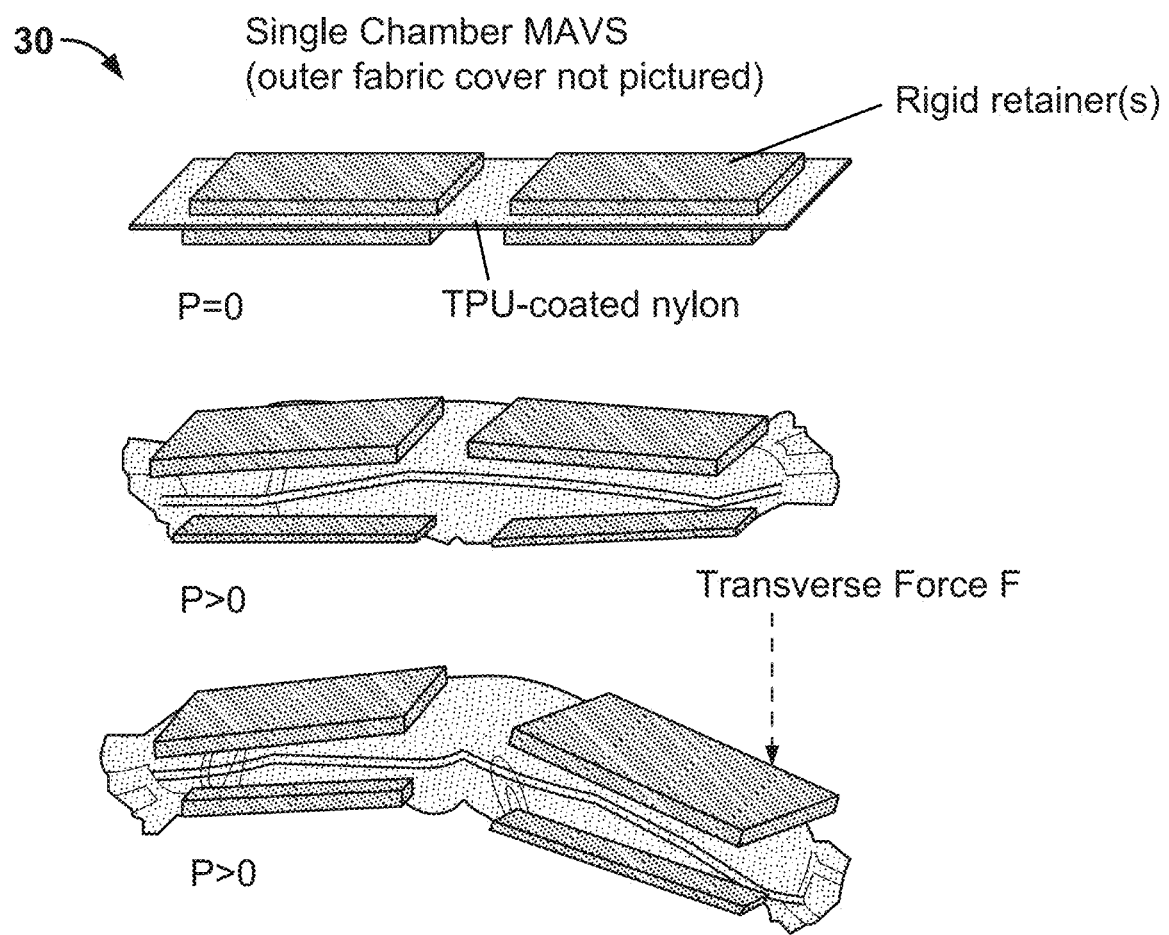

For example, FIGS. 7, 8A-8F, and 9A-9C illustrate alternative support members 230, 330a-f, 430a-c (e.g., for use as the second support member 30 in FIG. 1, to provide inversion/eversion support) having a different total shape/size, different number of retaining members, etc. More specifically, as shown in FIG. 7, the support member 230 may include five retaining members 290 (or other numbers) supported by the first (top) side portion 254. With reference to FIGS. 8A-8F, the total length La-f of each support member 330a-f, respectively, may be varied (e.g, again with first, top side portions 354a-f having retaining members). With reference to FIGS. 9A-9C, a length Aa-c of each retaining member 490a-c may be varied.

Figure 4:
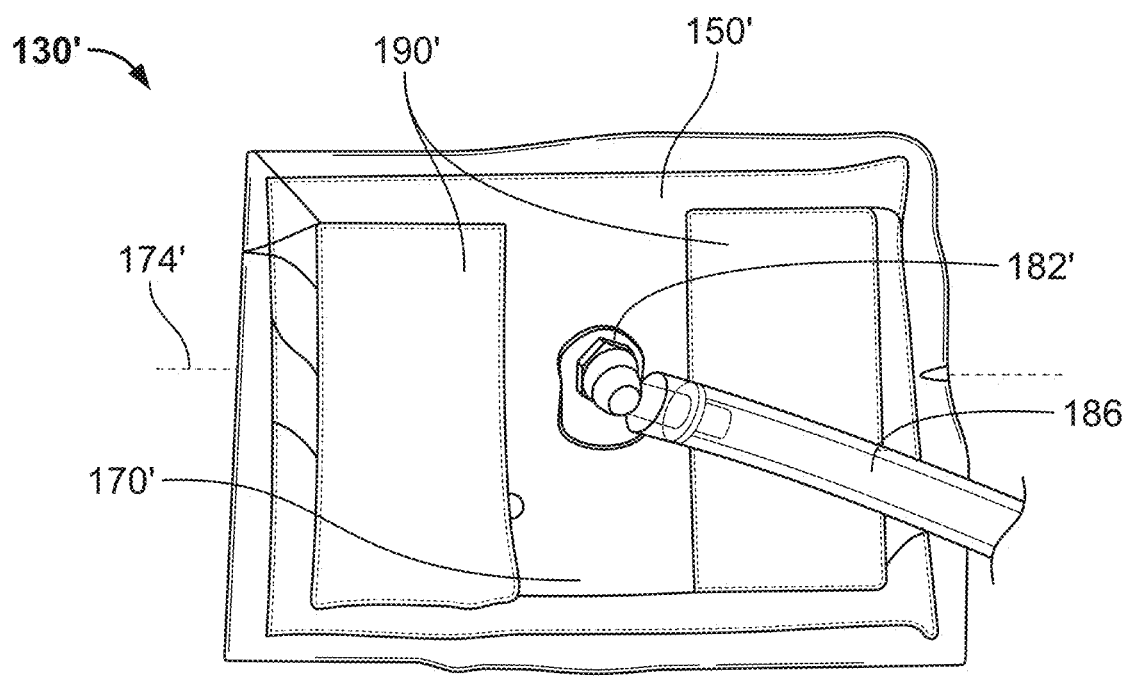
FIGS. 4-5 are top perspective views of an example of the support member of FIGS. 3A-3D, illustrating the support member in a deflated state (FIG. 4) and an inflated state (FIG. 5).
Figure 5:
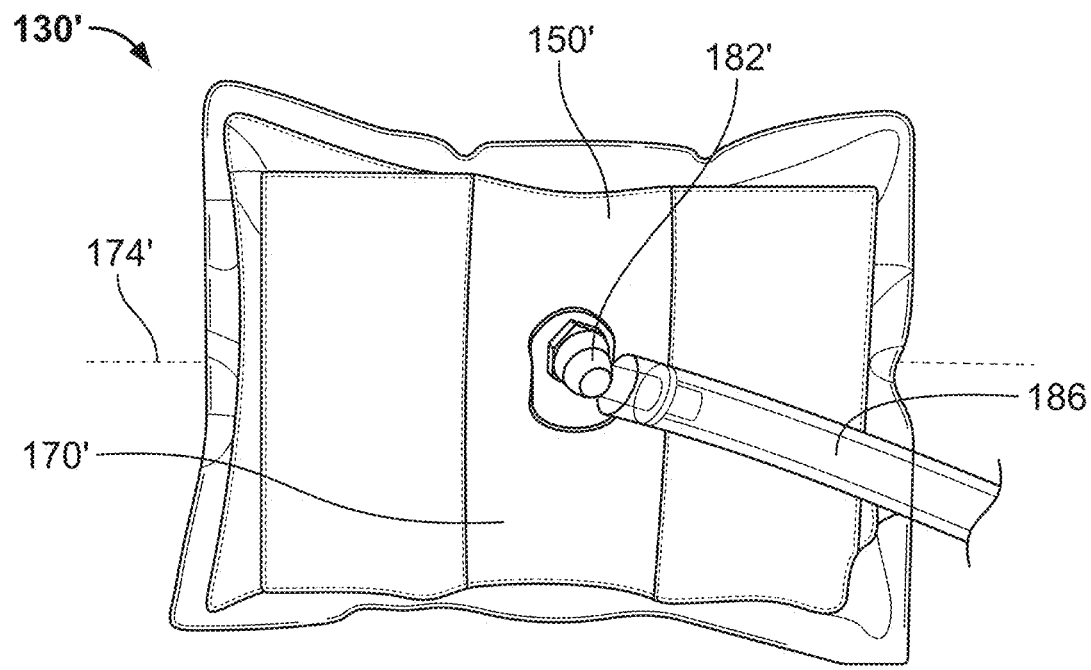

FIGS. 4-5 illustrate one example of the support member 130' of FIGS. 3A-3D. The support member 130' includes the body 150', the chamber 170', the plurality of retaining members 190', and the valve member 182'. The valve member 182' is connected to the hose 186. The support member 130' is adjustable between a first, deflated state (FIG. 4), in which movement (i.e., bending) of the body 150' is not restricted, and a second, inflated state (FIG. 5), in which the movement of the body 150' is restricted by a combination of the inflated chamber 170' and the retaining members 190'. In particular, when the support member 130' is in the first state, the support member 130' is more flexible than when the support member 130' is in the second state.

The support member 130' has limited flexibility when the support member 130' is in the second state. In particular, each section of the support member 130' between retaining members 190' along the longitudinal axis 174' forms a joint when the support member 130' is in the second state. The support member 130' has limited movement at each joint when the chamber 170' is inflated, but movement at each retaining member 190 is inhibited. In other words, a stiffness of the support member 130' is variable along the longitudinal axis 174'.

Figure 6H:
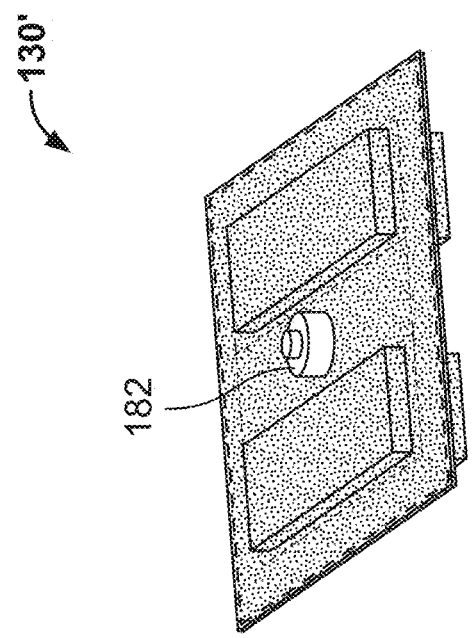

FIGS. 6A-6G illustrate one method of manufacturing the support member 130' of FIGS. 4-5. In particular, the method includes using thin pieces 195, 197, 199 of fabric or other material (e.g., two thin 2D homogeneous shells) to create each layer of the soft actuator, and in some embodiments using heat-sealing and/or stitching to connect and seal the layers. The retaining members 190 may be modeled using solid 3D homogeneous extrusions. In the illustrated embodiment, two thin pieces of fabric or other material 195 (FIG. 6A) are placed in an assembly and stacked vertically and sealed (e.g., heat-sealed) to create a seam around the perimeter, thereby creating the chamber 170 and defining a central main layer 194. As shown in FIG. 6D, two of the retaining members 190 (e.g., the top two retaining members) are placed on top of an additional piece of fabric or other material 197, and then covered (e.g., encased) with a further piece of fabric or other material 199 to create a top main layer 196 (e.g., forming the first side portion 154). The other two retaining members 190 (e.g., the bottom retaining members) are similarly placed on a piece of fabric or other material 197, and then covered (e.g., encased) with a further piece of fabric or other material 199 to create a bottom main layer 198 (e.g., forming second side portion 158). A sewing machine may be used to stitch around a perimeter of the three main layers 194, 196, 198 to hold the retaining members 190 in place, as well as to hold the main layers 194, 196, 198 together (FIGS. 6E and 6H). In some embodiments a global interaction property for surface-surface contact is applied to the assembly.

More specifically, as shown in FIGS. 6A-6C, the first, inflatable chamber layer 194 (central, main layer) may be fabricated from two pieces 195 of thermoplastic polyurethane (TPU) coated nylon fabric (e.g., 200 Denier Rockywoods Fabrics) which is thermally bonded with a 2 mm heat impulse sealer (e.g., AIE-500 2 mm Impulse Sealer, American International Electric INC, CA) which applies uniform heat and pressure to the seam to create an air-tight seal. In the illustrated embodiment, the inflatable chamber layer 194 is sealed at the designated location to create a rectangular shape using the impulse sealer on three of the four sides. The fourth side is left open for the installation of the valve member 182 (e.g., pneumatic fitting). A first hole 192 (FIG. 6B) is cut into the fabric to form the inlet 178, and the valve member 182 (e.g., threaded nylon barbed nozzle and nut fitting) is secured onto the TPU coated nylon (FIG. 6C). The final, fourth side is then sealed with the impulse sealer to create an air-tight seal that is the same net shape as the entire support member 130'.

With reference to FIGS. 6D-6H, in the illustrated embodiment each of the two outer layers 196, 198 includes rigid Polylactic Acid (PLA) 3D Printer Filament (e.g., 1.75 diameter mm PLA 3D Printer Filament, HATCHBOX®) sewn between two pieces of fabric or other material 197, 199. In particular, the retaining members 190 are 3D printed using PLA and have a thickness of 2 mm and a width of 40 mm. In the illustrated embodiment, each of the constraining (top and bottom) layers 196, 198 are made from two pieces of nylon fabric material 197, 199, which are stacked with the rigid retaining members 190 placed in between at predetermined distances (FIG. 6D). Other embodiments include different types of materials for the various pieces of material that form the layers 194, 196, 198.

Figure 6G:
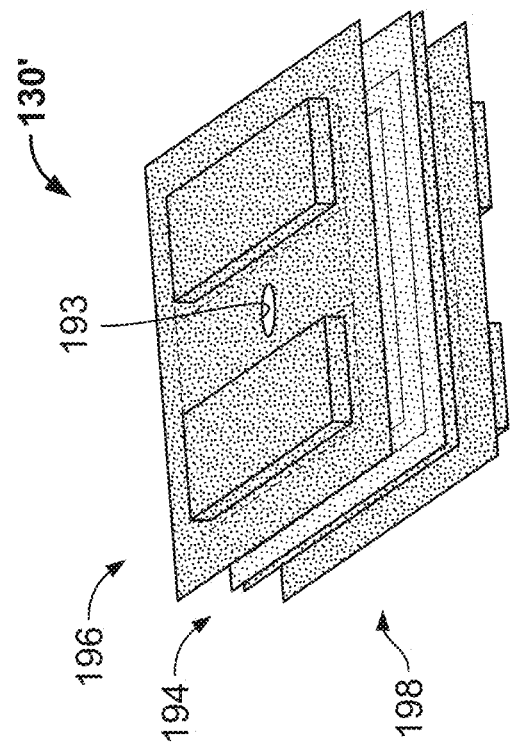

Once the layers 194, 196, 198 are arranged, in the illustrated embodiment a sewing machine (e.g., SE-400 Brother, Bridgewater, N.J.) may be used to create a stitched seam around the net shape of the retaining members 190, thereby encasing the respective retaining members 190 between the two pieces of nylon fabric material 197, 199 that form the respective layer 196, 198 (FIG. 6E). This is done to create each of the top and bottom layers 196, 198 (i.e., first and second side portions 154, 158). A second hole 193 (FIG. 6F) is then cut into the top layer 196 to allow the valve member 182 (e.g., tube fitting) to fit in between the retaining members 190 when assembled. The central, inflatable chamber layer 194 is then placed in between the two constraining layers 196, 198 as shown in FIG. 6G, with the valve member 182 centered within the second hole 193 cut previously into the top constraining layer 196. A final seam is then sewn in a rectangular shape around the retaining members 190 at an offset distance (e.g., at a 5 mm offset). This offset seam may provide a buffer to avoid sewing into the central, sealed chamber layer 194, and to provide an offset distance that constrains the expansion (e.g., in the vertical direction from the frame of reference of FIG. 6H) of the chamber 170 during inflation. Other embodiments include different locations for seams than that illustrated, as well as different numbers of seams. In some embodiments, one or more of the seams may be replaced by other attachment methods of structures (e.g., heat-sealing, etc.)

As such, the fabrication of the support member 130' includes a three layer laminate that has different levels of stiffness based on the orientation of the rigid outer layers 196, 198. The sealed, central inflatable chamber layer 194 is secured between the top and bottom layers 196, 198 of rigid retaining members 190 embedded in fabric material 197, 199. The retaining members 190 may be aligned on the top and bottom of the soft actuator. By integrating relatively smaller retaining members 190 into a compliant fabric actuator, the rigid retaining members 190 in the outer top and bottom layers 196, 198 act as retainers that reduce the total volume of the actuator when inflated, thereby constraining the actuator so that it will be flush with the user's body part (e.g., ankle) while inflated. Incorporating relatively smaller rigid retaining members 190 may achieve greater stiffness while not inhibiting user comfort or gait.

The following paragraphs describe testing of the support member 30 to determine the stiffness of the support member 30 as specific parameters (e.g., length A of retaining members 190, total length L, etc.) are varied.

First, two main parameters were varied and evaluated using equations: (1) the lengths A (FIG. 3B) of the retaining members 190 and (2) the size of a gap D (FIG. 3B) between the retaining members 190 exposing the inflated chamber 170. In particular, three different lengths A were chosen and tested: 1 cm, 2 cm, and 3 cm (these values were chosen mainly for fabrication and practicality restrictions). The second parameter, D, was varied from 0.5 cm to 3 cm in increments of 0.5 cm. It was limited to 0.5 cm in the lower bound for fabrication purposes, as the tube fitting (e.g., valve member 182) could not be inserted into a smaller gap D. The upper bound of the parameter was also set to 3 cm, as going beyond this gap size may increase the volume beyond what is desired for fast inflation. Based on the equations, it was determined that a support member 30 with retaining members 190 having a relatively smaller length A showed increased resistance to transverse loads than a support member 30 with the same gap D and retaining members 190 having relatively larger lengths A.

A finite element analysis (FEA) software was used during testing, to predict the accuracy of an analytic model and to validate a behavior of the stacked materials. The FEA simulation was run in a dynamic explicit environment. Two thin 2D homogeneous shells were used to create each layer of the fabric actuator and stacked vertically, and sectioned partitions of the shell faces were tied to create the heat-sealed seams. The rigid pieces were modeled using solid 3D homogeneous extrusions. The TPU coated nylon was simulated using a Young's Modulus of 498.9 MPa, a Poisson's ratio of 0.35, and a material thickness of 0.15 mm. The PLA rigid pieces were modeled using material properties with a Young's Modulus of 3600 MPa and a Poisson's ratio of 0.3. The two thin shells were placed in an assembly and stacked vertically and sealed to create a seam around the perimeter. The rigid pieces were placed on the top and bottom faces of the actuator at a pre-defined gap distance as shown in FIGS. 10A-10E. Finally, another thin 2D homogeneous shell was placed to encase the soft actuator and rigid pieces. The outward faces of the rigid pieces were tied to the outer shell and a global interaction property for surface-surface contact was applied to the assembly. A solid 3D homogeneous clamp was created from the PLA material property and fixed at Tx=Ty=Tz=0 to hold the actuator at a fixed point for the cantilever beam example modeled in the previous section.

With continued reference to FIGS. 10A-10E, a clamp was created to hold the support member 30 at a fixed point to form a cantilever beam. Two loads were applied: (1) a uniform pressure load to the internal faces of the support member 30, and (2) a transverse load applied at a fixed point at the end of the support member 30. A total of three steps were run for the simulation: (1) Pressurization, (2) Stabilization, (3) Point Load as depicted in FIGS. 10A-10E. The deflection of the support member 30 (referred to as MAVS in the images) was measured by fixing one half of the MAVS along the y-axis, and applying a perpendicular force to the free end. Deflection was measured as the change in the angle from the starting position of the inflated actuator to the final position of the free end of the MAVS as shown in FIGS. 10A-10E. A transverse load of 5 N, 10 N, 15 N, and 20 N was applied at a fixed point on the free end of the actuator, which was inflated to 100 kPa. This was done for the three highest performing MAVS from sets A-C predicted by the analytic model. The deflection of the end of the actuator was measured along the same axis as the transverse load for MAVS sets A1-A3, B1-B3, and C1-C3. The results indicated the same behavior as the parameters of the length A of the retaining members 190 and the size of the gap D were varied. In particular, as the size of the gap D was increased, the stiffness of the support member 30 decreased. This behavior was also seen in the length A of the retaining member 190, with decreasing resistance to deflection as the retaining member 190 increased in length. FIGS. 11-17 provide further illustrations of the support member 30, in both an inflated and deflated state, and showing for example the FEA analysis that was conducted on the different areas of the support member 30.

Furthermore, a universal tensile testing machine (UTM) (Instron 5565, Instron Corp., High Wycombe, United Kingdom) was also used to measure the stiffness and deflection for the support member 30 with variable retaining member lengths A and/or variable gap sizes D. In particular, the support member 30 was evaluated experimentally using a UTM that displaced the free end of the support member 30 when fixed as a cantilever beam. The experimental results showed that the most effective support member 30 was the support member 30 having retaining members 190 having a length A of 1 cm and a gap size D of between 1 cm and 1.5 cm. More specifically, the support member 30 having the length A of 1 cm and gap size D of 1 cm required and observed force of 26.71±0.06 N at 100 kPa, and the support member 30 having the length A of 1 cm and gap size D of 1.5 cm required and observed force of 22.74±0.2 N at 100 kPa. As such, this support member 30 had the highest stiffness values when active, and lower stiffness values when passive. Accordingly, it was determined after testing that the support member 30 with retaining members having a length L of 1 cm and a gap D of exposed inflatable chamber 170 of 1 cm may be best suited for use in the ankle support assembly 10 of FIG. 1. Additionally, it was determined that a support member 30 with smaller gaps D and smaller retaining member lengths A provided the greatest stiffness.

Overall, the support member 30 is designed to be integrated, for example, into the ankle support assembly 10 (e.g., soft robotic ankle-foot orthosis (SR-AFO) exosuit as shown in FIG. 1). The support member 30 is pneumatically actuated using a soft fabric actuator, which increases inversion-eversion ankle stiffness when actuated, but with minimal influence in dorsiflexion-plantarflexion stiffness. The increased inversion-eversion ankle stiffness may inhibit or prevent ankle buckling while walking and may correct gait irregularities with use.

Still further, having a rigid retaining member 190 positioned relative to the sealed, inflatable chamber 170 will restrict the total volume of the chamber 170. And limiting the boundaries of the chamber 170 during inflation and restricting the expansion in at least one direction (e.g., in the vertical direction) may result in higher stiffness at smaller volumes, thereby allowing for faster actuation time.

Figure 19:
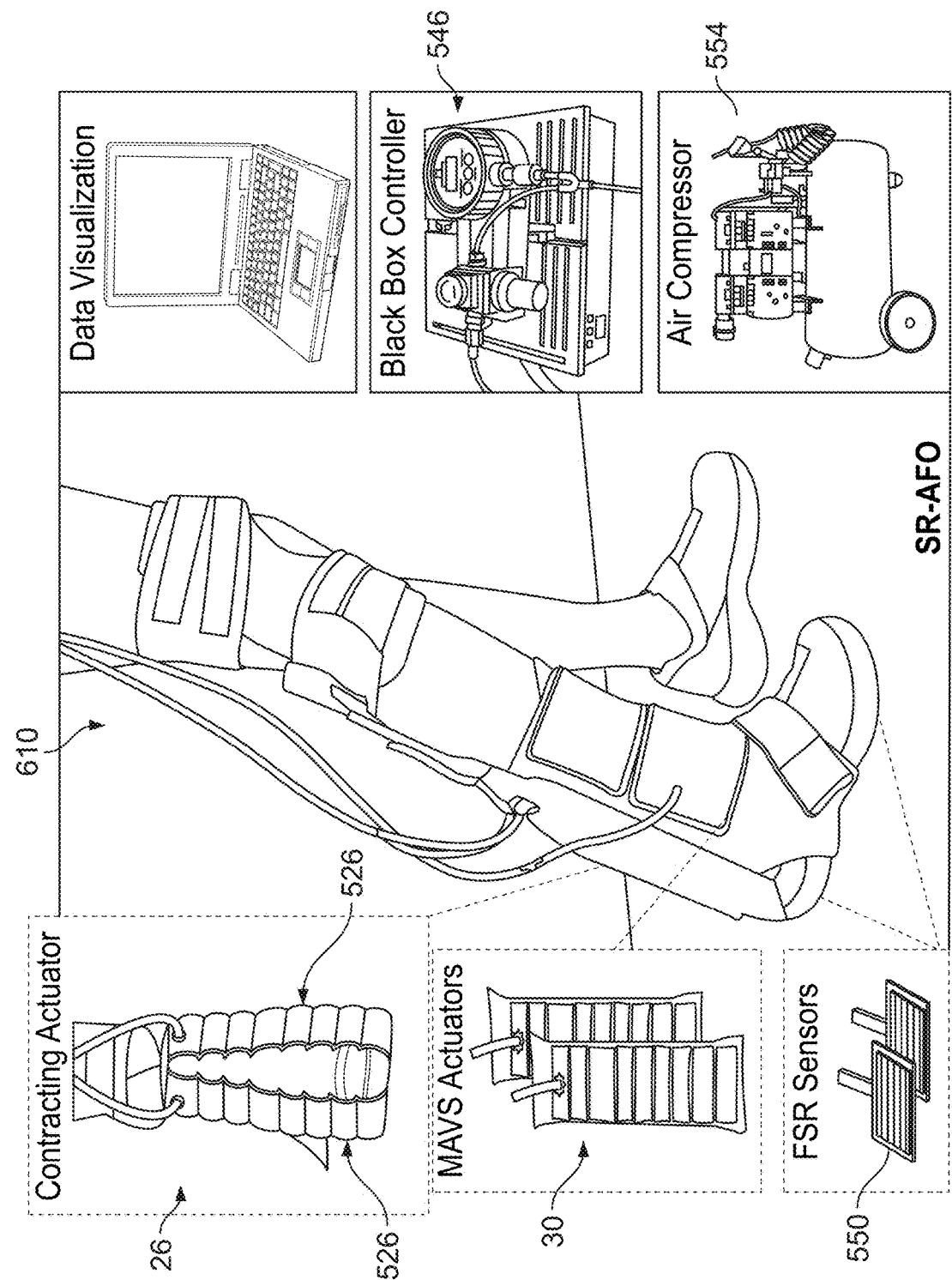
FIG. 19 is a perspective view of an ankle support assembly according to another embodiment, having support members for both inversion/eversion support as well as plantarflexion support.

As described above, and as illustrated in FIG. 1, in some embodiments the ankle support assembly includes a support member or members 26 along a back of the leg (e.g., along a back of the calf) that may be used to support plantarflexion. Such a support member may be in addition to, or separate from, the support member or members 30 described above that are located along a side of the ankle and provide support for inversion/eversion (e.g., support members 130, 130', 230, 330, 430 described above). FIGS. 18A-18B illustrate an embodiment of an ankle support assembly 510 that includes a support member or members 526 (e.g., for use as the support member 26) that are used along the back of the leg to support plantarflexion. FIG. 19 illustrates another embodiment of an ankle support assembly 610 that includes both the support member or members 526, as well as a support member or members 30 (e.g., support members 130, 130', 230, 330, 430 described above).

Figure 20:
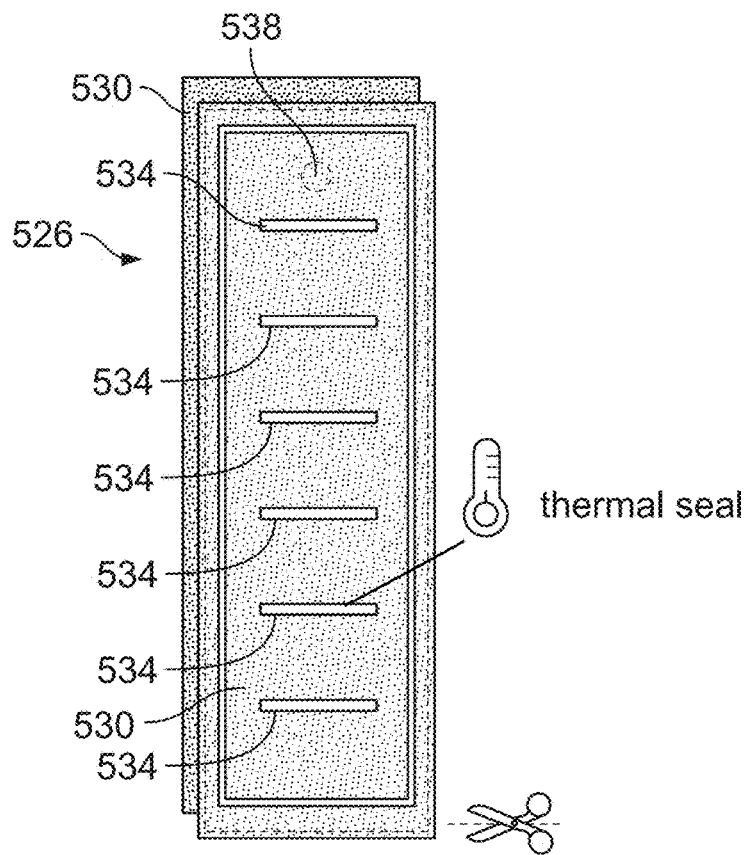
FIGS. 20-25, 26A-26B, 27A-27C, and 28-30 are perspective and schematic views of the support member of FIGS. 18A-18B that provides plantarflexion support, including illustrations of testing that was conducted on the support member, as well as views of additional components for use with the ankle support assemblies described herein.
Figure 21:
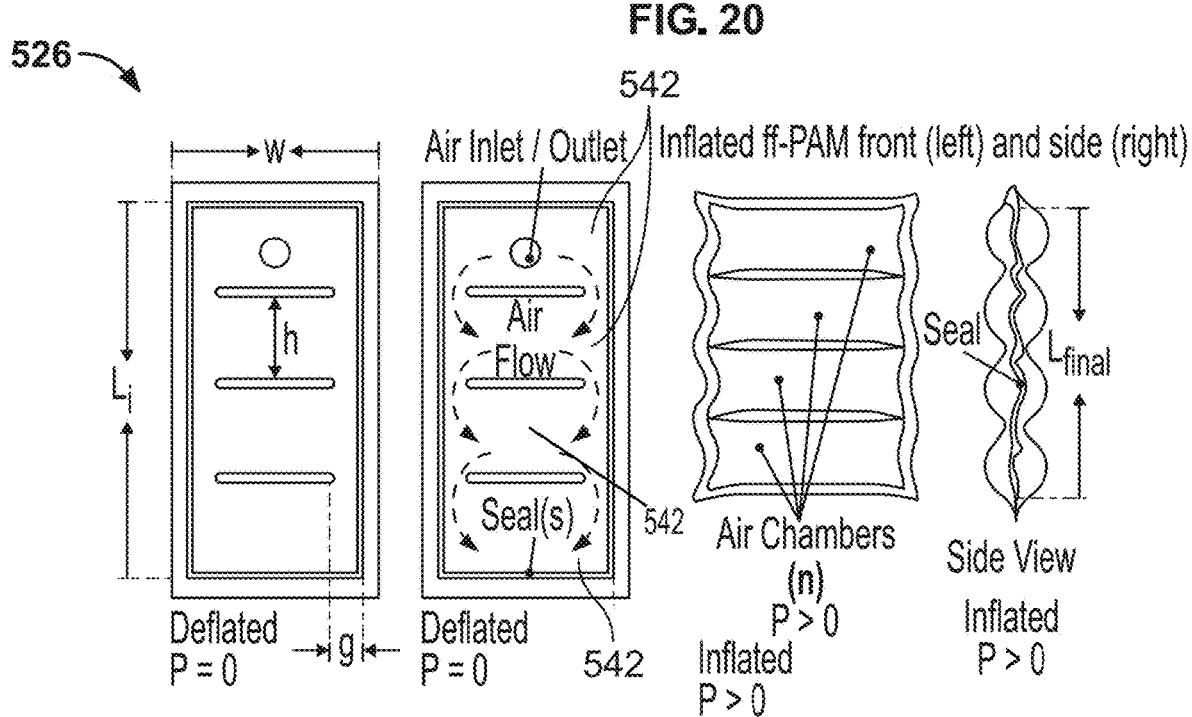
Figure 22:
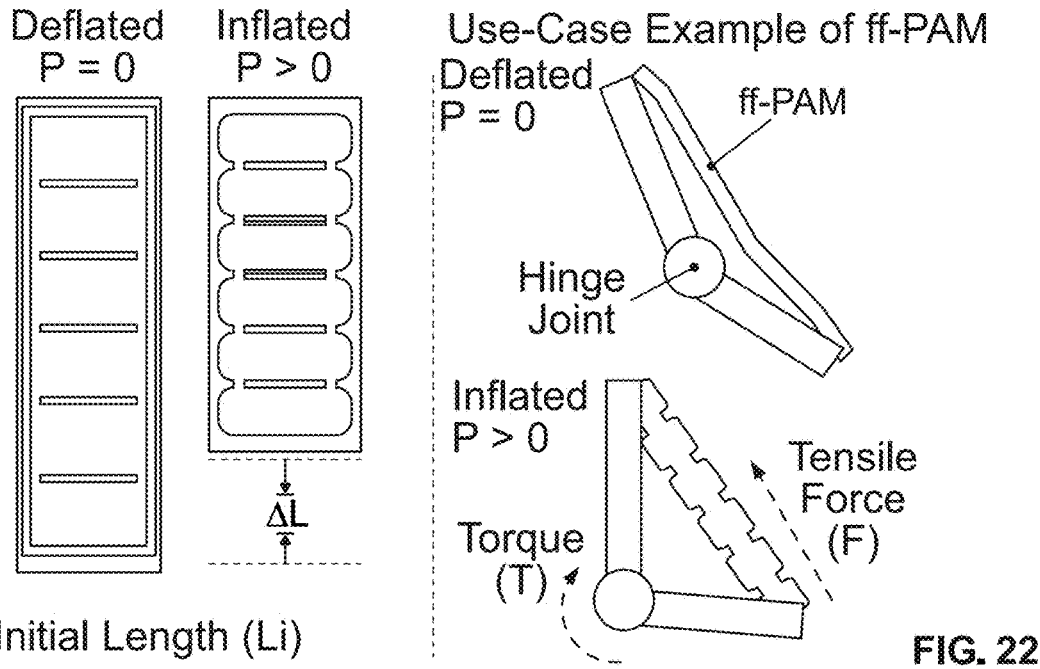
Figure 23:
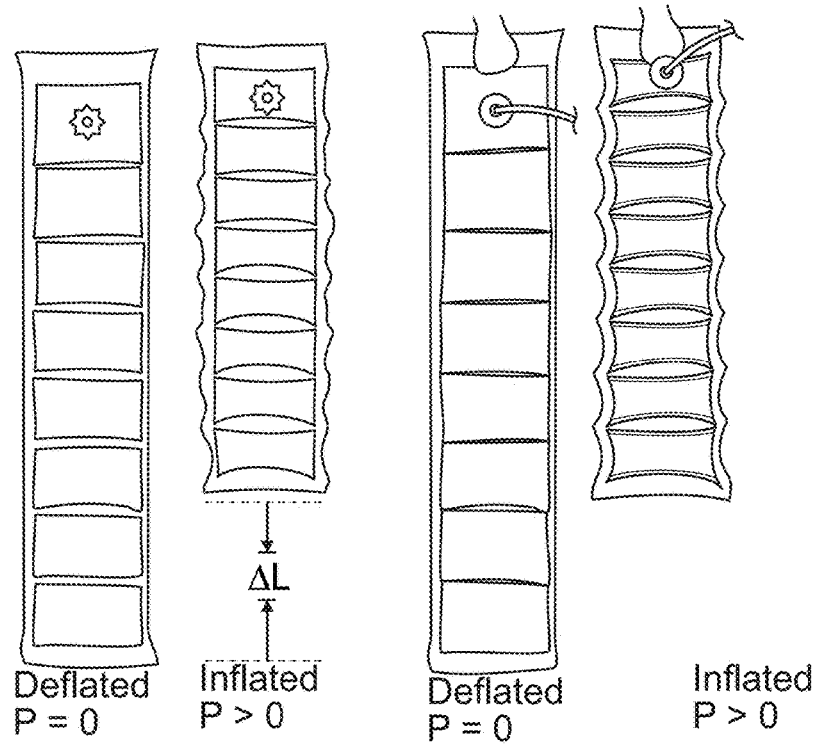

FIGS. 20 and 21 illustrate one embodiment of the support member 526 seen in FIGS. 18A-18B and 19 for supporting plantarflexion. The support member 526 is formed from two soft fabric layers 530 (e.g., TPU coated nylon fabric) that are coupled together along an outer perimeter (e.g., by sewing). The two layers are then also heat sealed at a plurality of spaced-apart heat seal locations. In the illustrated embodiment, six heat seals 534 are provided. Each is a thin, generally horizontal strip, extending parallel to each of the other parallel heat seals 534. The overall support member 526 has an elongate, rectangular shape, although other embodiments include different sizes and shapes than that illustrated, as well as different numbers and arrangements of heat seals 534. As illustrated in FIG. 20, the support member 526 also includes an opening 538 formed in one of the fabric layers 530 for insertion of a fitting and/or inflation tube/tether. With reference to FIG. 21, when inflated, the air flows around the heat seals 534 and inflates the space between the two soft fabric layers 530 forming air chambers 542 (e.g., four air chambers). Each of the heat seals 534 is spaced from another heat seal 534 by a height "h" and each of the support members 526 has an overall length "L" and overall width "w.". As seen in FIG. 21, as well as in FIGS. 22 and 23, when the support member 526 is inflated, the overall length "L" decreases (creating a contraction).

The support members 526 (also referred to as ff-PAM in the images) have a low profile when active and inactive. When deflated, the support members 526 lay flat at the thickness of the material (e.g., 5 mm). When inflated, the air chambers 542 expand outward to generate a contracting motion and tensile force. In the illustrated embodiment, the fabrication of these soft actuators uses a thermoplastic polyurethane (TPU) coated nylon fabric (200 Denier Rockywoods Fabrics) which is thermally bonded using a heat impulse sealer to apply uniform heat and pressure. This creates an air-tight seal between the interfacing, TPU coated faces of the nylon with a width of 2 mm. The low profile makes the wearable assembly less cumbersome and creates an ease of application in different rehabilitative settings. The lightweight materials prevent unwanted alterations to the user's kinematics during natural gait from becoming strewn by restricted motion or added weight.

Figure 24:
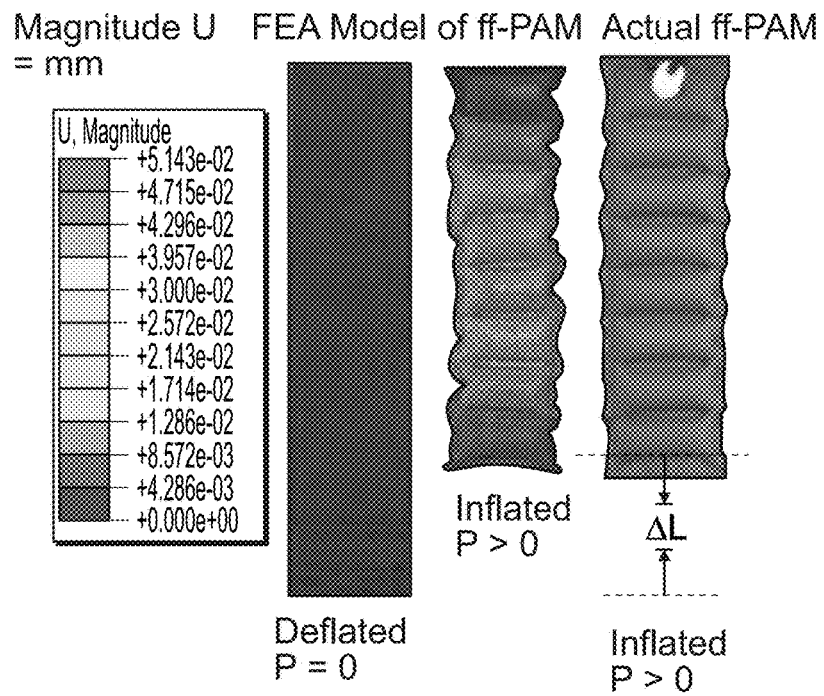
Figure 25:
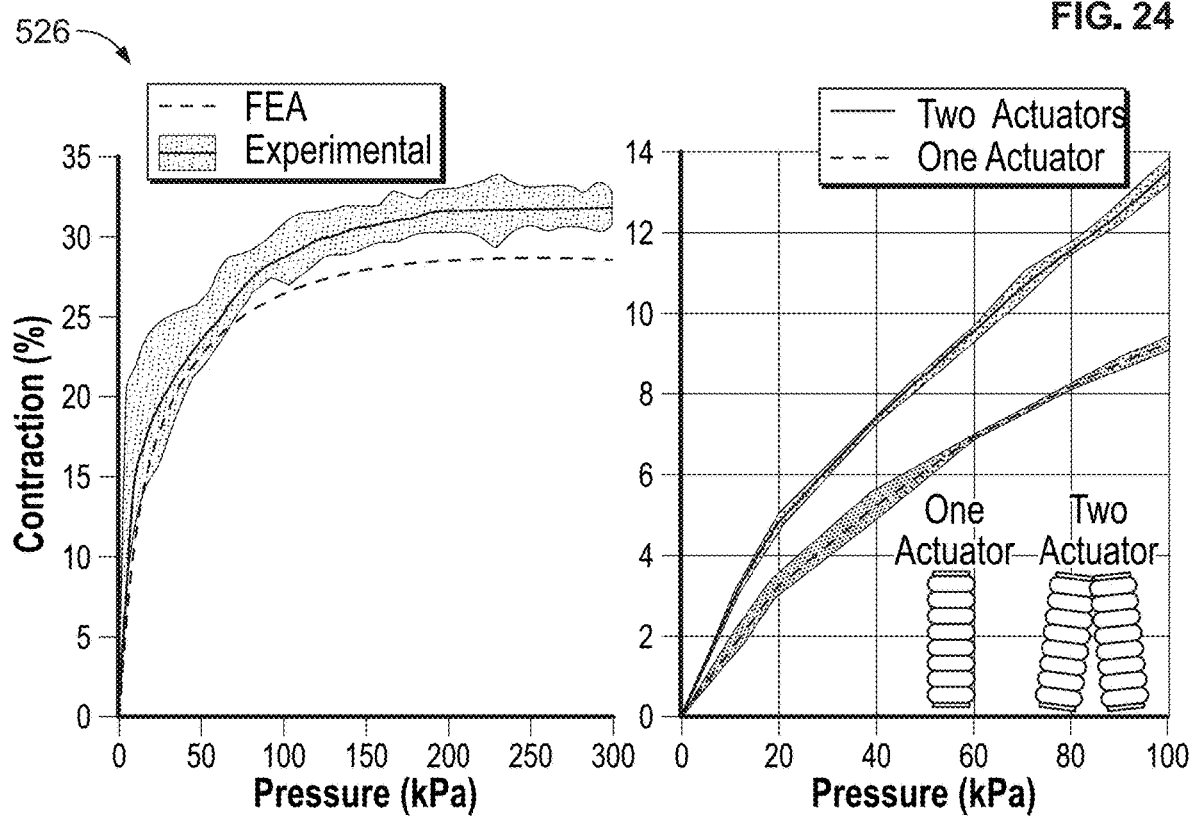

With reference to FIGS. 24 and 25, the support members 526 were modeled and tested in ideal conditions and fixed boundary conditions through finite element analysis (FEA) and testing on a universal testing machine using rigid vice grips in perfectly fixed positioning. The contraction percentage was optimized using FEA. The deflated length (initial length) of the support member 526 was compared to the inflated length, which is a function of pressure, the height "h" of each air chamber 542, and the number "n" of air chambers 542. For this work, eight air chambers 542 were selected to achieve the desired contraction, though any number can be selected for a functional support member 526. As contraction is a function of overall length, the selected length was sufficient to pull the ankle to the desired angle.

With reference to FIGS. 18A-18B and 19, in some embodiments two support members 526 may be provide along the back of the leg. During testing, it was found that the addition of such a second support member 526 showed a significant increase (e.g., 45% in one instance) of payload capacity. The two support members 526 may also be angled relative to one another. For example, in some embodiments the support members 526 are angled at 5 degrees relative to one another. This angle was found to produce the highest pulling force. Other embodiments may include different angles or ranges of angles, including angles greater than 5 degrees (e.g., 10 degrees, 15 degrees, 20 degrees, 25 degrees, 30 degrees, etc.). It was also found during testing that the gastrocnemius (GA) and soleus (SOL) muscle activity during late stance is reduced by 13.4% and 16.6% respectively.

Figure 26B:
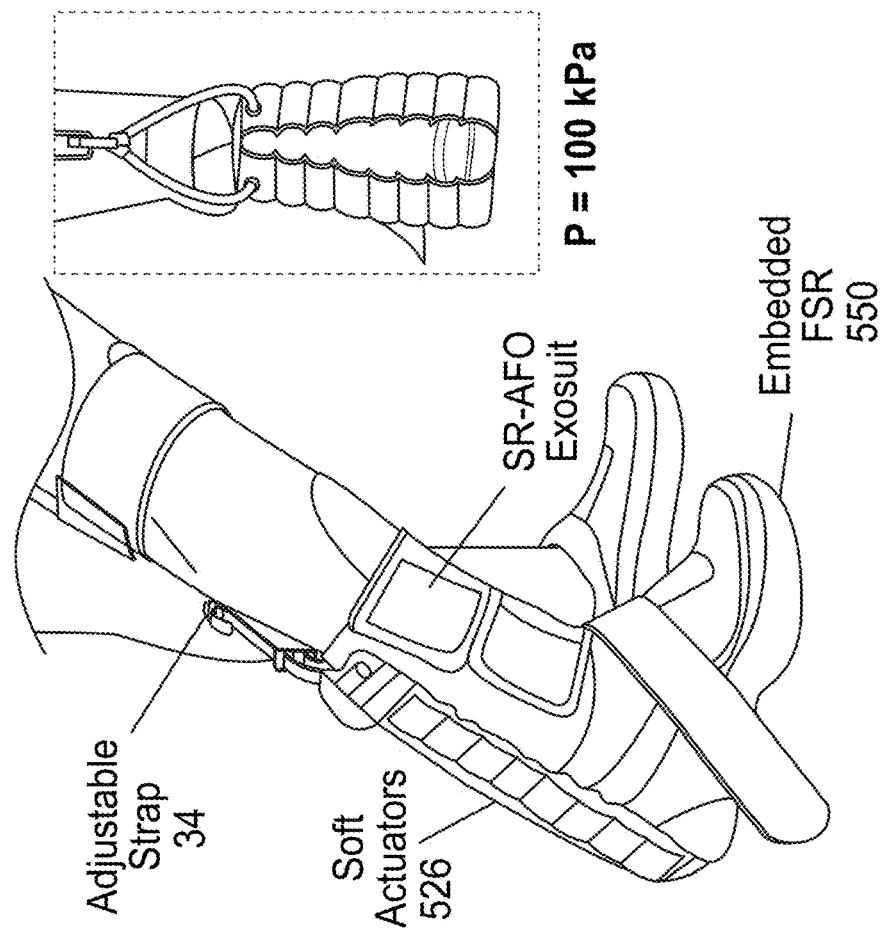
Figure 26A:
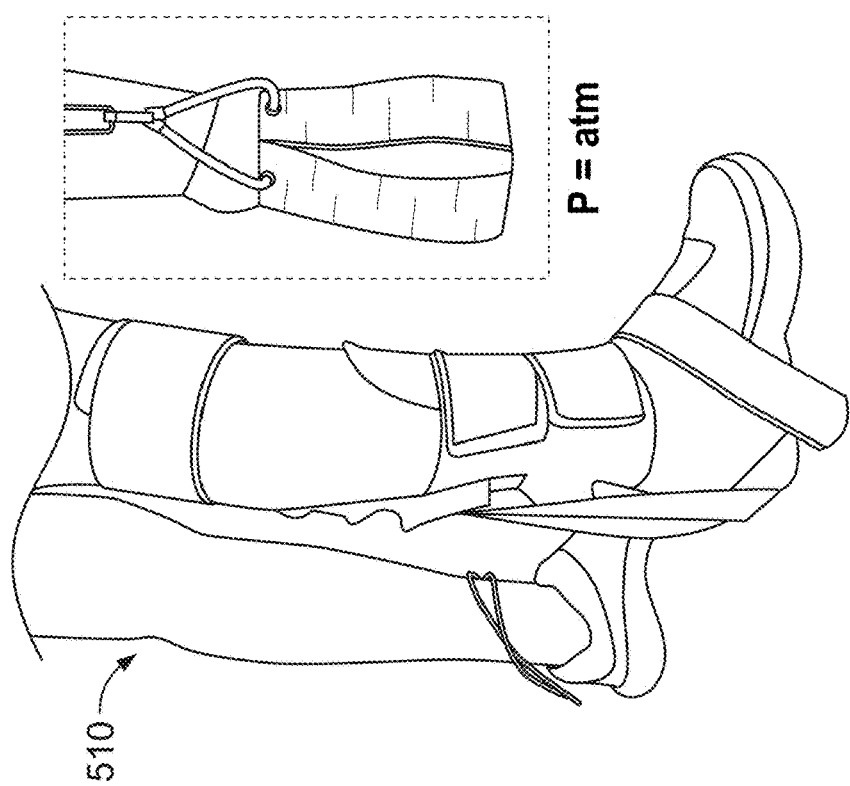

With reference to FIGS. 26A-26B, the ankle support assembly 510 (as well as assembly 10 or 610 referenced above) may function as an exosuit, and assist ankle plantarflexion by utilizing the intrinsic compliance of the fabric-based design paired with pneumatic actuators anchored at specific points on the body. The ankle support assembly 510 has a low profile and fits tightly around the user's foot and lower leg. The low profile makes the wearable robot less cumbersome and creates an ease of application in different rehabilitative settings. The lightweight materials prevent unwanted alterations to the user's kinematics during natural gait from becoming strewn by restricted motion or added weight. In some embodiments, the ankle support assembly (e.g., assembly 10, 510, or 610) includes layers of neoprene and spandex, and straps with hook and loop fasteners are provided to secure the overall assembly over the foot, around the ankle, and below the knee (seen in FIGS. 26A-26B).

Figure 27A:
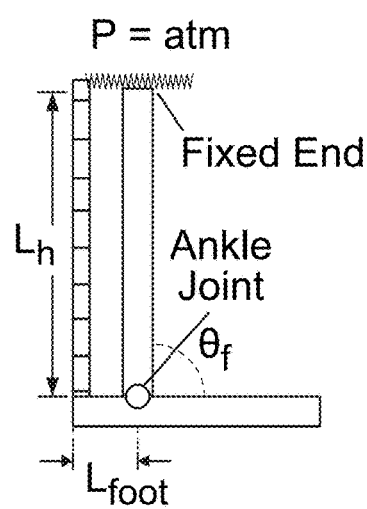
Figure 27B:
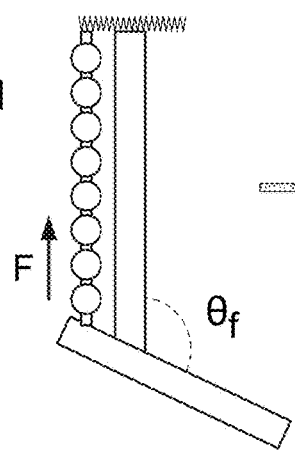
Figure 27C:
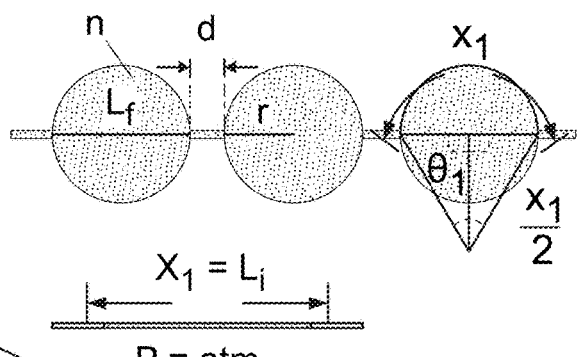

As seen in FIGS. 27A-27C, during development a maximum force output of the ankle support assembly 510 was modeled, illustrating a lever force produced to assist in plantarflexion.

Figure 28:
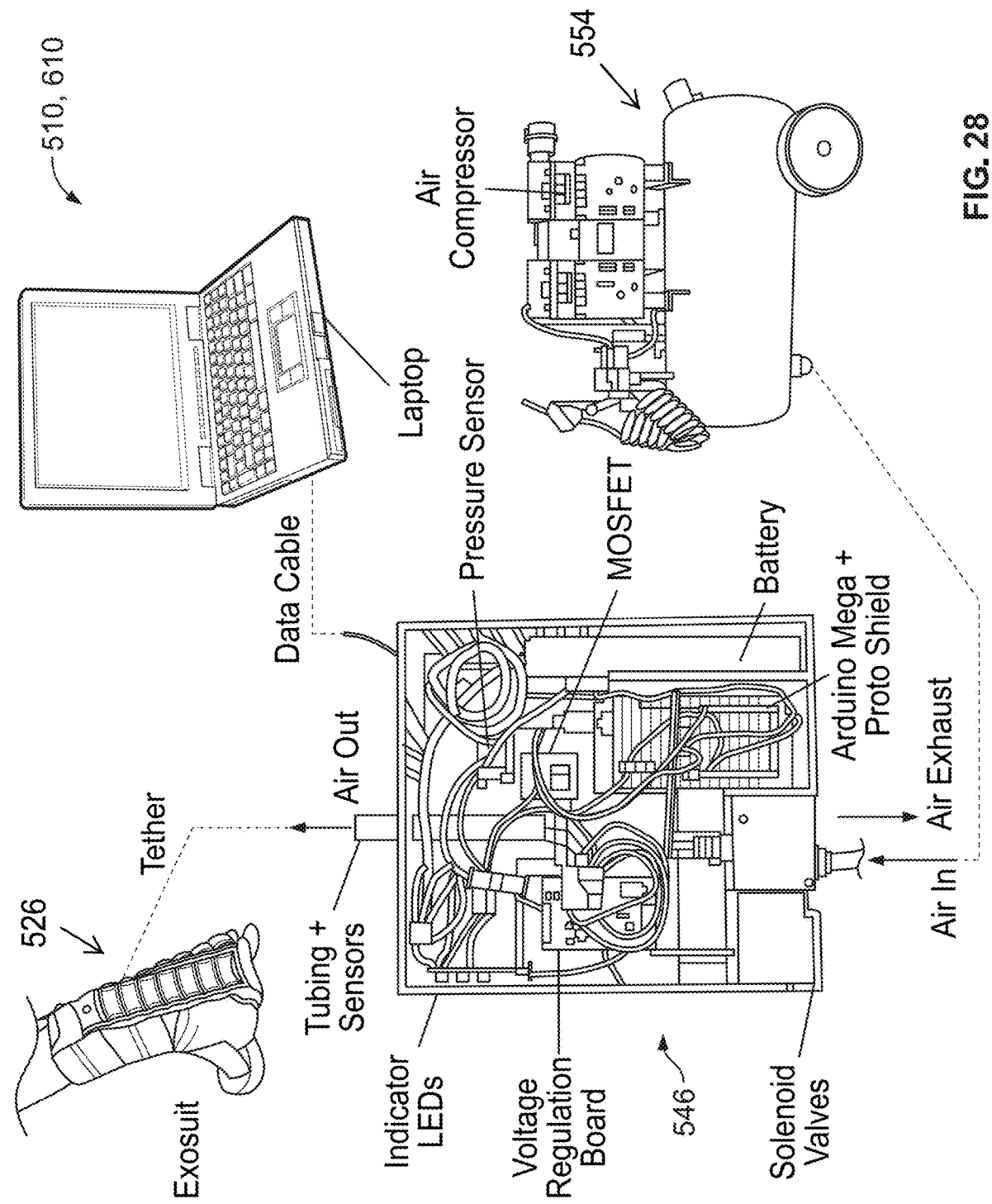

With reference to FIGS. 19 and 28, the ankle support assembly 510 (as well as assembly 10 or 610) may include a control box 546 that runs electro-pneumatic hardware, and a controller for the logic behind synchronizing the timing of the support member or members 26, 30 with the user's gait cycle. In some embodiments the ankle support assembly 10, 510, or 610 may include pressure sensors, valves, and/or the controller, which is used to collect data from force-sensitive resistor (FSR) sensors 550 to indicate when to pressurize the support members (e.g., support members 130' and/or 526) during walking. In the illustrated embodiment, the FSR sensors 550 (FIG. 19) are embedded in the user's shoes, in the front and back, to detect where the foot is in the gait and when contact with the ground has been made. The support member or members 526 run along the back of the user's calf and pulls the heel upward, producing a negative angle from a neutral position. In the illustrated embodiment, the controls and hardware for the ankle support assembly 10, 510, or 610 are not carried or worn by the user, although in other embodiments one or more of the controls and hardware may be carried by a user.

With continued reference to FIG. 28, in the illustrated embodiment the control box 546 houses a logic controller fitted with a ProtoShield to connect and read analog signals from force-sensitive resistor (FSR) sensors 550. The FSR sensors 550 are embedded in the user's shoe at the anterior and posterior ends of the shoe insoles to provide kinematic data information that is critical to time-events to detect heel strike and the weight shift preceding pre-swing. A 12V, 5000 mAh LiPo Battery is used to power the assembly. A custom voltage regulator board is used to step the voltage down to 5V to power both the logic board and the pressure sensors, which monitor the resulting pressure throughout operation. A portable air compressor 554 is used to provide a pneumatic actuation source and is controlled through the use of 3-way, 2-channeled solenoid values, which activate during specified times in the human gait cycle to provide instantaneous pressure to the support members 526 through the tether. The valves are powered through MOSFETs which connect the signal from the logic controller to the 12V power rail. The housing of the control box 546 is made from a custom 3D printed PLA design to house all of the electro-pneumatic components. LEDs are used as indicators once the lid of the control black box 546 is closed to provide information to the user regarding the current state or status of the assembly. A power switch is provided on the side of the box 546 to shut down the assembly and safely disconnect from battery power when not in use.

Figure 29:
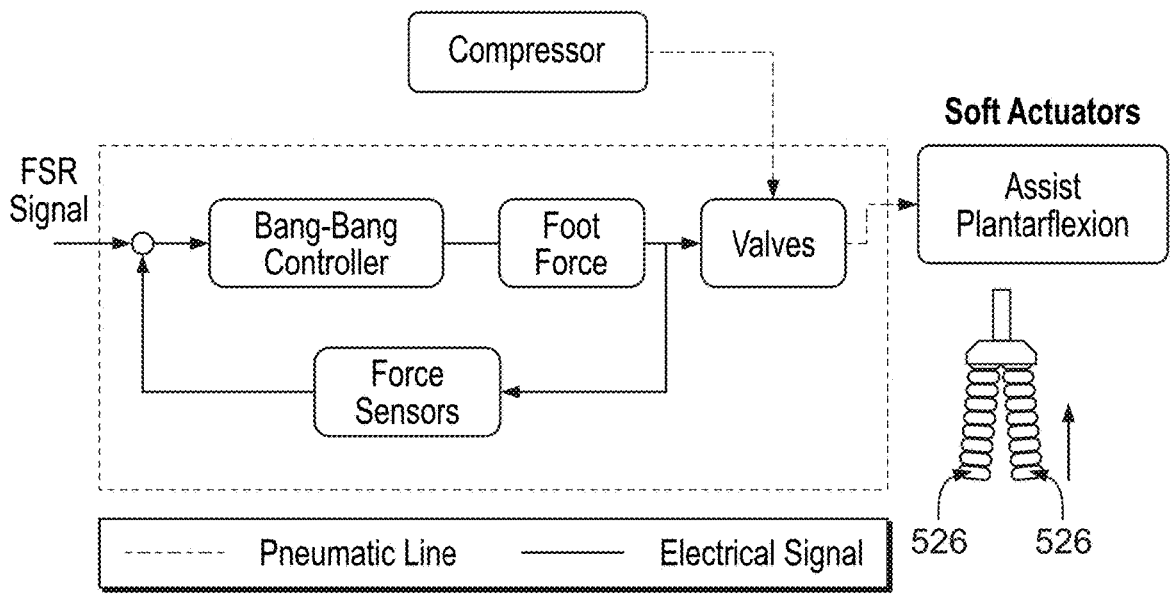
Figure 30:
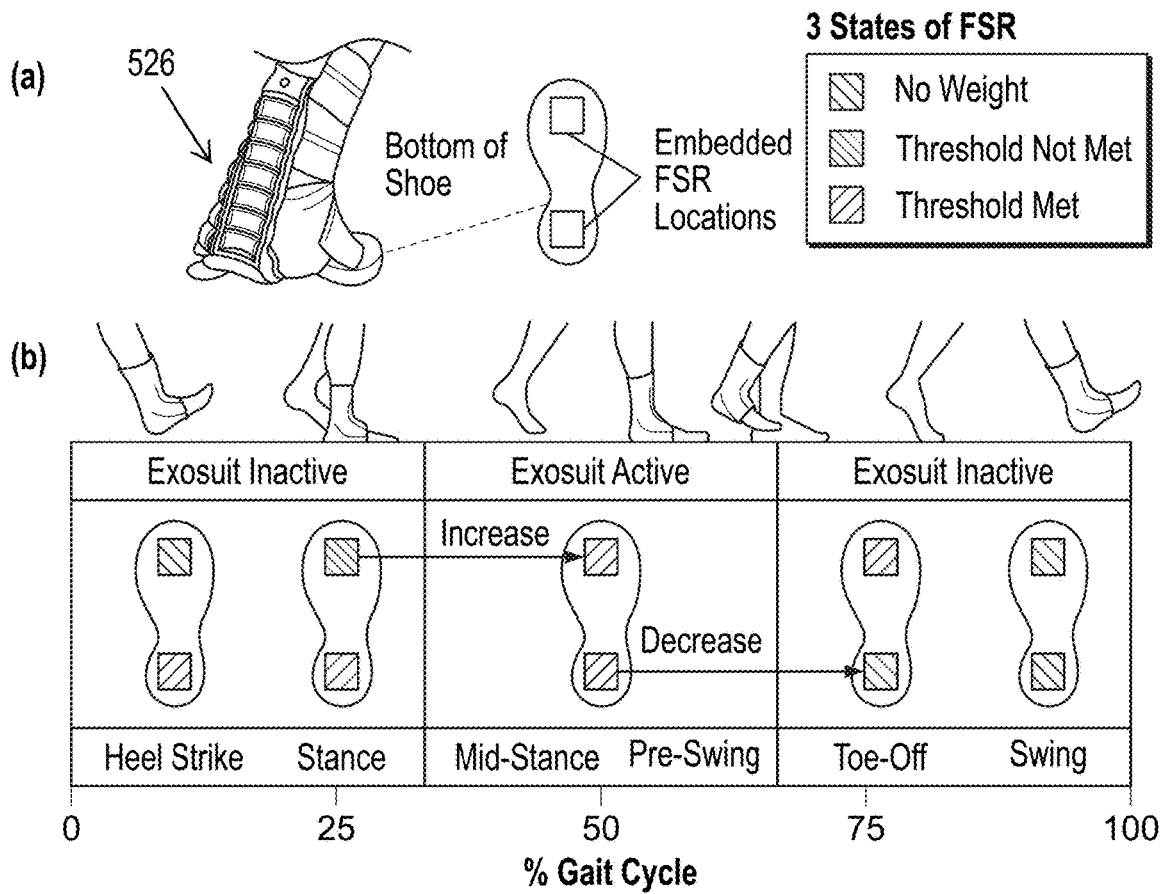

FIG. 29 illustrates an example of controller logic for the controller of the box 546, and FIG. 30 illustrates human testing that was conducted. During the human testing, EMG (electromyography) sensors and a wireless goniometer were used to monitor the muscle activity and kinematics of the ankle joint. The actuators were inflated during the window of late stance (40%-60% of the gait cycle). During this window, a reduction of 13.4% was seen for the GA (gastrocnemius) muscle, and 16.6% for the SOL (soleus). Controller logic is based on bang-bang control, based on input from the FSR, producing inflation in the actuator when the FSR passes a threshold. As illustrated in FIG. 30, during a single gait cycle (going from heel strike to heel strike), a threshold may be reached prior to the active range of the actuator which spans from mid-stance to pre-swing.

Although certain aspects have been described in detail with reference to certain preferred embodiments, variations and modifications exist within the scope and spirit of one or more independent aspects as described.

What is claimed is:

1. An ankle support assembly comprising:
   a body including a plurality of fabric layers, the body extending along a longitudinal axis;
   a sealed, inflatable chamber defined by the body;
   a valve member supported by the body and in fluid communication with the chamber; and
   a plurality of retaining members positioned relative to the chamber, wherein the retaining members are separate elements from the body, and are embedded within the fabric layers, wherein the retaining members are spaced apart from each other, wherein the retaining members are configured to limit expansion of the chamber in at least one direction,
   wherein the retaining members are positioned relative to the chamber such that the body has a variable stiffness along the longitudinal axis when the chamber is inflated,
   wherein the longitudinal axis extends centrally through the chamber, wherein the retaining members include a first retaining member positioned on a first side of the chamber and on a first side of the longitudinal axis, and a second retaining member positioned on a second, opposite side of the chamber and on a second, opposite side of the longitudinal axis, wherein a gap extends through the chamber between the first retaining member and the second retaining member along a direction perpendicular to the longitudinal axis, wherein the first retaining member and the second retaining member are positioned such that as the chamber expands, the gap is configured to increase, and the first and second retaining members are configured to move laterally away from one another along the direction that is perpendicular to the longitudinal axis.

2. The ankle support assembly of claim 1, further comprising:
   a frame;
   a support member positionable by the frame relative to an ankle of a user, the support member including the body, the inflatable chamber, the valve member, and the plurality of retaining members,
   wherein the support member is configured as a fabric-based actuator, and
   wherein the support member is configured to provide support in at least one directional movement of the ankle.

3. The ankle support assembly of claim 2, wherein the support member is a contracting soft actuator configured to support plantarflexion.

4. The ankle support assembly of claim 2, wherein the support member is a soft actuator configured to support inversion/eversion.

5. The ankle support assembly of claim 2, wherein sections of the support member between the plurality of retaining members along the longitudinal axis form joints when the chamber is inflated.

6. The ankle support assembly of claim 1, further comprising a tube or hose coupled to the valve member.

7. The ankle support assembly of claim 1, wherein each of the plurality of retaining members is a rigid member, wherein the plurality of retaining members are configured to limit the expansion of the chamber in at least one direction when the chamber is being inflated.

8. The ankle support assembly of claim 1, wherein the longitudinal axis is orientated such that the longitudinal axis is configured to extend lengthwise along a user's leg when the ankle support is worn.

9. The ankle support assembly of claim 1, wherein each of the plurality of retaining members is rectangular in shape.

10. The ankle support assembly of claim 1, wherein each of the plurality of retaining members is identical in size.

11. An ankle support assembly comprising:
- a first, inflatable support member configured to provide inversion / eversion support for an ankle, the first support member formed from first layers of fabric and having at least one rigid retaining member coupled to the first layers of fabric, the first support member having a body that defines a chamber, wherein the retaining member is a separate element from the body, and is embedded within the first layers of fabric;
- a second, inflatable support member configured to provide plantarflexion support for the ankle, the second support member formed from second layers of fabric and having heat seals that form air chambers along the second support member; and
- a third, inflatable support member configured to provide plantarflexion support for the ankle, the third support member formed from third layers of fabric and having additional heat seals that form additional air chambers along the third support member;
- wherein the second support member is configured to be angled at a non-zero angle relative to the third support member.

12. The ankle support assembly of claim 11, further comprising:
- a frame, wherein the first support member and the second support member are each positionable by the frame relative to the ankle.

13. The ankle support assembly of claim 12, further comprising:
- an anchoring strap configured to be positioned on a user's knee, and a connecting member extending between the anchoring strap and the first support member.

14. The ankle support assembly of claim 12, wherein the frame includes a pocket, and wherein the second support member is received in the pocket.

15. The ankle support assembly of claim 11, wherein the first support member includes the body having a first side portion, a second side portion, a first end portion, and a second end portion, wherein the first end portion extends between the first side portion and the second side portion, wherein the second end portion extends between the first side portion and the second side portion, wherein the first side portion and the second side portion and the first end portion and the second end portion define the chamber therebetween, wherein the chamber is configured to receive a fluid.

16. The ankle support assembly of claim 15, wherein the first support member includes a longitudinal axis extending through the first end portion and the second end portion of the body, wherein the body is elongated along the longitudinal axis.

17. The ankle support assembly of claim 15, wherein the second support member is angled at 5 degrees relative to the third support member.

18. The ankle support assembly of claim 15, wherein the retaining member is a first retaining member, wherein the first support member includes a second retaining member, wherein the first support member includes the chamber, wherein a longitudinal axis extends centrally through the chamber, wherein the first retaining member is positioned on a first side of the chamber and on a first side of the longitudinal axis, and the second retaining member is positioned on a second, opposite side of the chamber and on a second, opposite side of the longitudinal axis, wherein a gap extends through the chamber between the first retaining member and the second retaining member along a direction perpendicular to the longitudinal axis, wherein the first retaining member and the second retaining member are positioned such that as the chamber expands, the gap is configured to increase, and the first and second retaining members are configured to move laterally away from one another along the direction that is perpendicular to the longitudinal axis.

* * * * *